US006451937B1

(12) United States Patent
Hartwig et al.

(10) Patent No.: US 6,451,937 B1
(45) Date of Patent: Sep. 17, 2002

(54) SELECTIVE, CATALYTIC, THERMAL FUNCTIONALIZATION OF PRIMARY C-H HYDROCARBON BONDS

(75) Inventors: John F. Hartwig, New Haven, CT (US); Thomas Carl Semple, Friendswood, TX (US); Huiyuan Chen, New Haven, CT (US)

(73) Assignees: Shell Oil Company, Houston, TX (US); Yale University, New Haven, CT (US)

( * ) Notice: Subject to any disclaimer, the term of this patent is extended or adjusted under 35 U.S.C. 154(b) by 0 days.

(21) Appl. No.: 09/516,897

(22) Filed: Mar. 1, 2000

(51) Int. Cl.$^7$ .............................. C08F 4/44; C08F 10/00; C07F 15/00
(52) U.S. Cl. ........................... 526/126; 526/282; 556/9; 556/13; 556/12; 556/11
(58) Field of Search ................................ 556/9, 13, 12, 556/11, 126, 282

(56) References Cited

U.S. PATENT DOCUMENTS

| | | | |
|---|---|---|---|
| 5,059,701 A | 10/1991 | Keipert | 556/13 |
| 5,089,536 A | 2/1992 | Palazzotto | 522/16 |
| 5,321,106 A | 6/1994 | LaPointe | 526/126 |
| 5,527,929 A | 6/1996 | Timmers et al. | 556/7 |
| 5,532,394 A | 7/1996 | Rosen et al. | 556/11 |
| 5,539,068 A | 7/1996 | Devore et al. | 526/126 |
| 5,541,349 A | 7/1996 | Wilson et al. | 556/10 |
| 5,543,480 A | 8/1996 | Patton et al. | 526/126 |
| 5,616,664 A | 4/1997 | Timmers et al. | 526/127 |
| 5,621,126 A | 4/1997 | Canich et al. | 556/9 |
| 5,703,187 A | 12/1997 | Timmers | 526/282 |
| 5,770,538 A | 6/1998 | Devore et al | 502/117 |

OTHER PUBLICATIONS

U.S. patent application Ser. No. 09/516,896, Hartwig et al., filed Mar. 1, 2000.

"Pentamethylcyclopentadienyl–rhodium and –iridium Complexes. Part VI. π–Arene, π–Cyclohexadienyl, and π–Pyrrolyl Complexes," by C. White and P. M. Maitlis, *J. Chem. Soc. (A)*, 1971, pp. 3322–3326.

"Pentamethylcyclopentadienyl–rhodium and –iridium and iridium Halides, Part II. Reactions with Mono–, Di–, and Tri–olefins," by K. Moseley, J. W. Kang, and P. M. Maitlis, *J. Chem. Soc. (A)*, 1970, pp. 2875–2883.

"Thermal substitution reactions of the heterodinuclear complex $CpFe(CO)_2Co(CO)_4$ with phosphorus ligands," by Xiaoqing song, Theodore L. Brown, *Inorganica Chimica Acta* 242 (1996) pp. 271–279.

"The reaction of $CpFe(CO)_2X(X=Cl, Br, I)$ with phosphines catalyzed by $[CpFe(CO)_2]_2$: evidence for an electron transfer chain catalysis mechanism," by Stephen L. Gipson, Ling–Kang Liu, Raul U. Soliz, *Journal of Organometallic Chemistry* 526 (1996) pp. 393–395.

"Formation and chemistry of the transient 17–electron compounds $CpFe(CO)L$ ($L=PMe_2Ph$, $PPh_3$)," by Inga Kuksis, Michael C. Baird, *Journal of Organometallic Chemistry* 527 (1997) pp. 137–143.

"Iron–rhodium complexes with a single bridging diphosphine ligand: the crystal structured of $[CpFe(\mu-CO)_2(\mu-dppm)RhI_2]$," by Ian Mansfield, Nagwa Nawar, Anthony K. Smith, Nicola C. Tong, *Journal of Organometallic Chemistry* 525(1996) pp. 255–258.

"Transition–Metal Boryl Complexes: Structure and Reactivity of $CpFe(CO)_2Bcat$ and $CpFe(CO)_2BPh_2$," John F. Hartwig and Susan Huber, *J. Am. Chem. Soc.* 115 (1993) pp. 4908–4909.

"Selective Functionalization of Alkanes by TransitionMetal Boryl Complexes," by Karen M. Waltz and John F. Hartwig, *Science*, vol. 277, Jul. 11, 1997.

"Stoichiometric and Catalytic B–C Bond Formation from Unactivated Hydrocarbons and Boranes," by Carl N. Iverson and Milton R. Smith, III, *J. Am. Chem. Soc.*, 121 (1999), pp. 7696–7697.

"First synthesis of bis[1,2,3]triazolo[1,5–b;5',1'–f][1,3,6] thiadiazepine derivatives by [2+1] condensation of 1,2, 3–thiadiazoles with vicinal diamines," by Natalya N. Volkova, Evgeniy V. Tarasov, Wim Dehaen, and Vasiliy A. Bakulev, Received (in Cambridge, UK) Sep. 16, 1999, Accepted Oct. 8, 1999.

"Reactions of Rhodium(v) Hydrido–Silyl Complexes with Butyl–lithium and with Lithium Triethylhydridoborate," by Jose Ruiz, Brian E. Mann, Catriona M. Spencer, Brian F. Taylor, and Peter M. Maitlis, *J. Chem. Soc. Dalton Trans* (1987) pp. 1963–1966.

"Organoboron Compounds. Part V. The Hydrolysis of Cyclic Phenylboronates," by R. A. Bowie and O. C. Musgrave, pp. 3945–3948.

"($\eta^5$–Pentamethylcyclopentadienyl)Rhodium and –Iridium Compounds," Submtted by C. White, A. Yates, and P. M. Maitlis, Checked by D. M. Heinekey, *Transition Metal Organometallics and Ligands*, pp. 228–234.

Tetrahydrido($\eta^5$–Pentamethylcyclopentadienyl)Iridium, Submitted by Thomas M. Gilbert and Robert G. Bergman, Checked by Joseph S. Merola, *Transition Metal Polyhydride Complexes*, pp. 19–22.

"A Study of Hydroboration of Alkenes and Alkynes with Pinacolborane Catalyzed by transition Metals," by Schubert Pereira and Morris Srebnik, *Tetrahedron Letters*, vol. 37, No. 19, (1996) pp. 3283–3286.

"Facile Intermolecular Activation of C–H Bonds in Methane and Other Hydrocarbons and Si–H Bonds in Silanes with the Ir(III) Complex Cp*(PMe₃)Ir(CH₃)(OTf)," by Peter Burger and Robert G. Bergman, *J. Am. Chem. Soc.*, 115, (1993) pp. 10462–10463.

(List continued on next page.)

*Primary Examiner*—Deborah C. Lambkin

(57) ABSTRACT

A process for the catalytic coupling of aliphatic or alkyl branched alicyclic hydrocarbons with a functionalizing reagent under thermal conditions to selectively functionalize the hydrocarbon at its primary C—H site.

106 Claims, No Drawings

OTHER PUBLICATIONS

"C–H Bond Activation by a rare Cationic Iridium Dinitrogen Complex. An Important Electronic Effect in the Chemistry of the Hydridotris(pyrazolyl)borate Ligand," by David M. Tellers and Robert G. Bergman, *J. Am. Chem. Soc.,* 122 (2000) pp. 954–955.

"Typical Procedure for the Hydroboration of Alkynes Using Pinacolborane," *J. Org. Chem.,* vol. 57, No. 12, (1992) pp. 3484–3485.

"Synthese, Struktur and Reaktivität der Ferriophosphonium-Salze $CpFe(CO)(L)(PPh_2CH_2R')BF_4$ (L=CO, $CH_3CN$, $P''Bu_3$; R'=PH, CN, COOEt, $PPh_2$, $SiMe_3$); Kristallstrukturen von $[CpFe(CO)_2PPh_2CH_2SiMe_3]BF_4$ und $[CpFe(PPh_2CH_2Ph)CpFe(CO)](\mu-CO)_2$," by Christian Klasen, Ingo–Peter Lorenz, Siegbert Schmid und Georg Beuter, *Journal of Organometallic Chemistry,* 428 (1992) pp. 363–378.

"Synthesis and Characterization of Rhodium(I) Boryl and Rhodium (III) Tris(Boryl) Compounds: Molecular Structures of $[(PMe_3)_4Rh(B(cat))]$ and fac-$[(PMe_3)_3Rh(B(cat))_3]$ (cat=1,2-$O_2C_6H_4$)," by Chaoyang Dai, Graham Stringer, Todd B. Marder, Andrew J. Scott, William Clegg, and Nicholas C. Norman, *Inorg. Chem.,* 36 (1997) pp. 272–273.

Oxidative Addition of boron–boron, boron–chlorine and boron–bromine bonds to platinum(0), by W. Clegg, F.J. Lawlor, G. Lesley, T.B. Marder, N.C.Norman, A.G.Orpen, M.J.Quayle, C.R.Rice, A.J.Scott, and F.E.S. Souza, *Journal of Organomettalic Chemistry* 550 (1998) pp. 183–192.

"Boron–boron bond oxidative addition to rhodium(I) and iridium(I) centres," by W. Clegg, F.J. Lawlor, T.B. Marder, P. Nguyen, N.C.Norman, A.G. Orpen, M.J. Quayle, C.R.Rice, E.G.Robins, A.J. Scott, F.E.S. Souza, G. Stringer, and G.R. Whittell, *J. Chem. Soc. Dalton Trans.,* 1998 pp. 301–309.

"Reactions of catecholborane wit iridium complexes: molecular structure of trans–IrHCI(CO)(Bcat) $(PPh_3)_2$," Stephen A. Westcott, Todd B. Marder, R. Thomas Baker, and Joseph C. Calabrese, *Canadian Journal of Chemistry,* vol 71, No. 7, Jul. 1993, pp. 930–936.

"Synthesis of Boryl Metal Complexes with Additional Agostic Stabilization by Hydroboration of Fischer Carbyne Complexes," by H. Wadepohl, U. Arnold, and H. Pritzkow, *Angew. Chem. Int. Ed. Engl.,* 36, No. 9, (1997) pp. 974–976.

"Five–Coordinate Ruthenium (II) and Osmium(II) Boryl Complexes," by Geoffrey J. Irvine, Warren R. Roper, and L. James Wright, *Organometallics,* 16 (1997) pp. 2291–2296.

"Transition–Metal–Catalyzed Addition of Catecholborane to α–Substituted Vinylarenes: Hydroboration vs Dehydrogenative Borylation," by Stephen A. Westcott and Todd B. Marden, *Organometallics,* 12 (1993) pp. 975–979.

"Synthesis and molecular structure of the paramagnetic Co(II) bis(boryl) complex $[Co(PMe_3)_3(Bcat)_2]$ cat=1, 2-$O_2C_6H_4$)," by Chaoyang Dai, Graham Stringer, John F. Corrigan, Nicholas J. Taylor, Todd B. Marder, and Nicholas C. Norman, *Journal of Organometallic Chemistry,* 513 (1996) pp. 273–275.

"Reactivity of Organoplatinum Complexes with $C_6H_4O_2B–BO_2C_6H_4$: Syntheses of a Platinum Diboryl Complex with, and without, Metathesis of Boron–Boron and Metal–Carbon Bonds," by Carl N. Iverson and Milton R. Smith, III, *J. Am. Chem. Soc.,* 117 (1995) pp. 4403–4404.

"Synthesis of endo–$Cp_2TaH_2(BO_2C_6H_4)$ and exo–$cp_2TaH_2(BO_2C_6H_4)$: Regioisomers of the First Tantalum Boryl Complexes," by Dean R. Lantero, Douglas H. Motry, Donald L. Ward, and Milton R. Smith, III, *J. Am. Chem. Soc.,* 116 (1994) pp. 10811–10812.

"C–H Activation and Functionalization of Unsaturated Hydrocarbons by Transition–Metal Boryl Complexes," by Karen M. Waltz, Clare N. Muhoro, and J. F. Hartwig, *Organometallics* 1999, 18, pp. 3383–3393.

"Functionalization of Alkanes by Isolated Transition Metal Boryl Complexes," by Karen M. Waltz II and John F. Hartwig, *J. Am. Chem. Soc.* 2000, 122, pp. 11358–11369.

"Reactivity of Tungstenocene with B–B and B–H Bonds versus C–H Bonds," by John F. Hartwig and Xiaoming He, *Angew. Chem. Int. Ed. Engl.* 1996, 35, No. 3, pp. 315–317.

SELECTIVE, CATALYTIC, THERMAL FUNCTIONALIZATION OF PRIMARY C-H HYDROCARBON BONDS

1. FIELD OF THE INVENTION

The field of the invention pertains to the selective functionalizing of a hydrocarbon at its primary C—H site by thermally reacting a functionalizing reagent and the hydrocarbon in the presence of an transition metal catalyst.

2. BACKGROUND OF THE INVENTION

Aliphatic compounds, and especially alkanes, are among the most abundant but least reactive molecules. Chemical synthesis relies on reactions that form one product selectively, and few reactions involving aliphatic compounds such as alkanes occur in this fashion. Radical reactions, such as halogenations and autoxidations, typically produce mixtures of products; even enzymes do not react regiospecifically with linear alkanes. Transition metal compounds are known to react with alkanes to give terminal alkyl complexes selectively, but these reactions are typically stoichiometric in metal. Transition metal-catalyzed dehydrogenation suffers from unfavorable thermodynamics and isomerization of terminal to internal alkenes during the reaction. Carbonylation of alkanes is also endothermic, and the photochemical processes produce secondary photoproducts.

Several years ago, it was reported in K. M. Waltz; C. N. Muhoro, J. F. Hartwig, Organometallics, 1999, 21 and in K. Waltz, J. F. Hartwig, Science 1997, 277, 211, that low valent transition metal complexes containing boryl ligands reacted with hydrocarbons, including alkanes, by photochemical dissociation of ligand to produce functionalized hydrocarbons. It was reported that organoboronate esters were formed in a stoichiometric fashion by the regiospecific replacement of one hydrogen on a terminal position with a boryl group. It was also reported in H.Chen, J. F. Hartwig, Angew.Chem.Int.Ed.Engl 1999 that commercially available $R_2BBR_2$ ($R_2$=pinacolate) reagents and substituted cyclopentadienyl (Cp*) Re(CO)$_3$ would catalytically convert alkanes to alkylboronate esters under photochemical reaction conditions. Photochemical processes, however, are impractical at an industrial scale.

It is desirable to functionalize regiospecifically an aliphatic compounds at its terminal C—H site. It is also desirable that the process for the functionalization occur thermally rather than through other means such as photochemical processes. It is also an object of the invention to manufacture a functionalized aliphatic compounds, and especially a functionalized alkane, by a process which is catalytic rather than stoichiometric in metal.

3. SUMMARY OF THE INVENTION

There is now provided a process for the catalytic coupling of aliphatic hydrocarbons with certain reagents under thermal conditions to selectively functionalize the aliphatic hydrocarbon at its terminal C—H site.

In one embodiment, there is provided a process for selectively functionalizing an aliphatic or alkyl branched alicyclic hydrocarbon at a primary C—H hydrocarbon bond comprising thermally reacting a functionalizing reagent and the hydrocarbon in the presence of a catalyst, said catalyst comprising:
  a) a source of a transition metal;
  b) a source of a 3 to 8, cyclic or non-cyclic, aromatic or non-aromatic, neutral, cationic or anionic, substituted or unsubstituted electron donor moiety which does not dissociate under thermal reaction conditions, wherein said moiety
    (i) lacks aromatic C—H bonds on the moiety directly bonded to the transition metal, or
    (ii) contains sterically hindered aromatic C—H bonds on the moiety directly bonded to the transition metal; and
  c) a source of ligands capable of formally donating an electron pair to the transition metal a) and which dissociate thermally;
and wherein said functionalizing reagent comprises a source of boron.

In another embodiment, there is provided a catalytic process having more than 50 turnovers comprising thermally activating said catalyst in the presence of a functionalizing reagent and an alipahtic or alkyl branched alicyclic hydrocarbon containing primary C—H bonds, said catalyst comprising:
  a) a source of a transition metal;
  b) a source of a 3 to 8, cyclic or non-cyclic, aromatic or non-aromatic, neutral, cationic or anionic, substituted or unsubstituted electron donor moiety which does not dissociate under thermal reaction conditions, wherein said moiety
    (i) lacks aromatic C—H bonds on the moiety directly bonded to the transition metal, or
    (ii) contains sterically hindered aromatic C—H bonds on the moiety directly bonded to the transition metal; and
  c) a source of ligands capable of formally donating an electron pair to the transition metal a) and which dissociate thermally;
and wherein said functionalizing reagent comprises a source of B, C, N, O, Si, P, S, Ge, As, Al, or Se.

In yet another embodiment of the invention, there is provided a functionalization process comprising selectively functionalizing 80% or more of primary C—H hydrocarbon bonds in a hydrocarbon composition in the presence of a thermally activated catalyst, wherein said process turns over the catalyst 50 or more times.

Preferably, the catalyst composition used in the process of the invention is comprised of, or obtained by combining a source of the following in any sequence:
  a) a source of a transition metal;
  b) a source of a 3 to 8, cyclic or non-cyclic, aromatic or non-aromatic, neutral, cationic or anionic, substituted or unsubstituted electron donor moiety which does not dissociate under thermal reaction conditions, wherein said moiety
    (i) lacks aromatic C—H bonds on the moiety directly bonded to the transition metal, or
    (ii) contains sterically hindered C—H bonds on the moiety directly bonded to the transition metal; and
  c) a source of ligands comprising trialkylsilanes, unsaturated aliphatic compounds, π allyl compounds, or π arene compounds, wherein said π arene compounds
    (i) lack aromatic C—H bonds on the moiety directly bonded to the transition metal, or
    (ii) contain sterically hindered aromatic C—H bonds on the moiety directly bonded to the transition metal.

A more preferred catalyst used in the process of the invention comprises, or is obtained by combining a source of the following in any sequence:
  a) Rh or Ir;
  b) a fully substituted cyclic $C_5$ moiety having a π-coordinated electronic structure and lacking aromatic C—H bonds; and c) ligands comprising aliphatic unsaturated or π arene compounds, and wherein said π arene compounds
 (i) lack aromatic C—H bonds on the moiety directly bonded to the transition metal, or
 (ii) contain sterically hindered aromatic C—H bonds on the moiety directly bonded to the transition metal.

There is further provided a functionalization process comprising selectively functionalizing 80% or more of primary C—H hydrocarbon bonds in a hydrocarbon composition in the presence of a thermally activated catalyst and a functionalizing reagent, wherein said functionalizing reagent comprises a compound containing a moiety represented by the following structure:

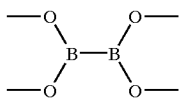

4. DETAILED DESCRIPTION OF THE INVENTION

The process of the invention is 80% or more selective toward functionalizing a primary C—H bond on hydrocarbon molecules, is catalytic, and relies ton thermal rather than photolytic or photochemical processes to supply the activation energy required for dissociating the ligand from the catalyst. The reaction proceeds in a straightforward manner in that a hydrocarbon, a catalyst, and a functionalizing reagent are contacted in a reaction vessel and heated to a temperature effective to activate the reaction towards the functionalization of the hydrocarbon at its primary C—H site. The nature of the catalyst and functionalizing reagent as described in further detail below enable one to manufacture selectively and thermally a hydrocarbon functionalized at its primary C—H site.

In the process of the invention, the hydrocarbon is functionalized at a terminal C—H bond in the presence of a catalyst and a functionalizing reagent. The catalyst used in the reaction must be one which is capable of being thermally activated, and the process functionalizes the terminal C—H bond of a hydrocarbon by thermally activating the catalyst. By thermal activation of the catalyst is meant the process of dissociating a c) ligand from a metal center by application of heat below the temperature at which the Z ligand (described below) dissociates from the metal center, and at least above the temperature of the environment at which the functionalizing reagent is stored.

A useful screening technique to determine whether a catalyst will activate a primary C—H bond is as follows. The catalyst one desires to employ is mixed with a deuterated ligand at a molar ratio within the range of 1:1 to 1:10 in the presence of an appropriate solvent, such as decane or cyclohexane-$d_{12}$. The mixture is analyzed by $^{31}$P NMR, $^{11}$B NMR, $^1$H NMR, and $^2$H NMR. The mixture is subsequently reacted solely by application of heat for 48 hours or less at no more than reaction pressures and at a temperature at which reaction takes place but below the temperature at which the b) moiety and c) ligands dissociate from the metal center. Analytical results of a catalyst which has been thermally activated will show the formation of a peak corresponding to free dissociated ligand and the formation of a deuterated catalyst, and the reduction or elimination of peaks corresponding to the presence of free deuterated ligand.

A useful screening test to determine whether a catalyst is one which is capable of being activated thermally is to conduct the reaction in the dark.

Although other compounds which chemically react to assist the dissociation of the c) ligand may be used along with the catalyst in the process of functionalizing an hydrocarbon, the catalyst used in the process must be of a type which is capable of being thermally activated in the absence of any compound which chemically reacts with the reagent to assist the activation of the reagent. Accordingly, a process which applies heat in addition to other activation mechanisms, such as chemical or photolytic means, and successfully activates the catalyst is nevertheless a process within the scope of the invention if the particular catalyst is capable of thermally functionalizing the hydrocarbon at a primary C—H bond in the absence of a co-catalyst or photons.

Other published catalytic systems for activating alkanes at the primary C—H bond require the presence of a sacrificial olefin to achieve high turnover numbers. An advantage of the process of the invention is that a sacrificial hydrogen acceptor is not required to provide a catalytic process with high turnover. Hydrogen released from the primary C—H hydrocarbon bond does not readily react with the functionalized hydrocarbon under reaction conditions. Although the presence of hydrogen acceptors is not excluded from the invention, the process of the invention is capable of achieving high turnover numbers in the absence of a sacrificial hydrogen acceptor.

By a "functionalizing reagent" is generically meant to include any compound as described below which operates to functionalize a hydrocarbon's primary C—H bond, and is not meant to define the reaction mechanism, efficiency, or fate of the reagent compound itself.

Suitable hydrocarbon substrates which are functionalized in the process of the invention are any hydrocarbons containing a primary C—H bond, also known as its terminal C—H bond. By "functionalized" is meant the replacement of H at a primary C—H bond of a hydrocarbon with the functionalizing reagent residue. By a primary C—H bond is meant any bond between a hydrogen atom and any carbon atom bearing two or more additional hydrogen atoms. The primary C—H bond is to be distinguished from a secondary C—H bonding site wherein the carbon atom is a secondary carbon atom and any functional group replacing its hydrogen atom would be considered a secondary functional molecule. It is to be understood that a "bond" as used throughout the specification means a covalent bond, a complex, a coordination, or any other form of a linkage between the stated atoms.

A hydrocarbon which is functionalized in the process of the invention is a saturated or unsaturated, branched or unbranched, substituted or unsubstituted aliphatic hydrocarbon (e.g. alkanes or alkenes); or a saturated or unsaturated, substituted or unsubstituted, alkyl branched alicyclic compounds, each having at least one primary C—H bond, and which do not deactivate the catalyst at reaction temperatures. The hydrocarbons may be used singly or in mixture. The hydrocarbon composition contains aliphatic and/or alkyl branched alicyclic hydrocarbons, optionally mixed with other hydrocarbon molecules, such as aromatic compounds. The hydrocarbon composition preferably comprises at least 50 wt. % aliphatic or alkyl branched alicyclic hydrocarbons, preferably at least 75 wt. %, more preferably at least 90 wt. %, and most preferably at least 95 wt. % or more up to 100 wt. %.

The source of the hydrocarbon can be any commercial source available, such as from a refined crude oil source or a Fisher-Tropsch stream, and can be used in crude mixtures or at any level of refinement, any fraction containing alkanes, and at any purity. Further, any olefin having 3–30 carbon atoms, and their dimers or trimers are also useful hydrocarbons provided that the molecule has a terminal site having one saturated carbon atom. Alkyl branched alicyclic (e.g. branched cycloparaffins or cycloolefins) are also useful, so long as the alkyl group contains at least one saturated carbon atom containing a primary C—H bond site.

In one embodiment, the hydrocarbon comprises a linear or branched alkane (by definition, having no unsaturation, cyclic or aryl moieties attached). Suitable examples of alkanes include those having 1–32 carbon atoms, advantageously 3–24, and particularly 6–18 carbon atoms. Examples of linear hydrocarbons include n-hexane, n-heptane, n-octane, n-nonane, n-dodecane, n-tridecane, n-tetradecane, n-pentadecane, n-hexadecane, n-heptadecane, n-octadecane, n-nonadecane, n-eicosane, and the like. Examples of branched aliphatic hydrocarbons include 2,2,3,3-tetra-methylbutane, 2,2,4-trimethylpentane, n-tricontane, 2-methylbutane, 2-methylpentane, 3-methylpentane, 2-methylhexane, 3-methylhexane, 2-methylheptane, 3-methylheptane, 4-methylheptane, 2,2-dimethylbutane, 2,3-dimethylbutane, 2,2-dimethylpentane, 2,3-dimethylpentane, 4-dimethylpentane, 3,3-dimethylpentane, 2,2-dimethylhexane, 2,4-dimethylhexane, 2,5-dimethylhexane, 3,4-dimethylhexane, 2,3-dimethylheptane, other 2-methyl or ethyl-$C_6$–$C_{28}$ alkanes, mixtures thereof, and the like.

Examples of alkyl branched alicyclic hydrocarbons include methyl cyclohexane, methyl cyclooctane, ethyl cyclohexane, ethyl cyclooctane, isopropyl cyclohexane, and the like.

The hydrocarbon may contain heteroatoms within the hydrocarbon chain, such as oxygen or nitrogen. However, the number of heteroatoms is no more than 1 heteroatom for every 4 carbon atoms, preferably no more than 1 heteroatom for every 6 carbon atoms, and more preferably the hydrocarbon is free of heteroatoms.

The catalyst used in the process of the invention comprises:

a) a source of a transition metal;

b) a source of a 3 to 8, cyclic or non-cyclic, aromatic or non-aromatic, neutral, cationic or anionic, substituted or unsubstituted electron donor moiety which does not dissociate under thermal reaction conditions, wherein said moiety
  (i) lacks aromatic C—H bonds on the moiety directly bonded to the transition metal, or
  (ii) contains sterically hindered aromatic C—H bonds on the moiety directly bonded to the transition metal; and c) a source of ligands capable of formally donating an electron pair to the transition metal a) and which dissociate thermally.

Preferably, the source of c) ligands comprise trialkylsilanes, unsaturated aliphatic compounds, π allyls, or π arene compounds, wherein said π arene compounds
  (i) lack aromatic C—H bonds on the moiety directly bonded to the transition metal, or
  (ii) contains sterically hindered aromatic C—H bonds on the moiety directly bonded to the transition metal.

In an embodiment of the invention, the catalyst can be conveniently represented by any one of the following structures:

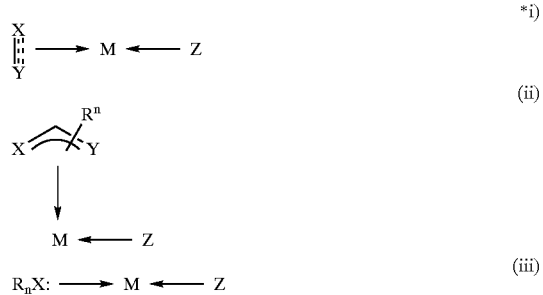

wherein X and Y together represent the c) ligands bonded directly or indirectly to M, and wherein X and Y may be bridged to form a cyclic arene compound which may contain branches, substituents, or fused aromatic rings; M represents the a) transition metal center; Z represents a cyclic or non-cyclic, aromatic or non-aromatic, neutral, cationic or anionic, substituted or unsubstituted compound having a n-coordinated electronic structure and lacking aromatic C—H bonds on the moiety which will directly bond to the transition metal a), R represents one or more optional substituents or branches, and n represents an integer ranging from 0 to 8. One or more of the ligands are bonded to the M metal center, and preferably more than one ligand is bonded to the metal center M. It is not critical to the invention that either the nature or location of the linkage between the ligands to the metal center be known, so long as some form of a linkage between the X or the X and Y ligands and the metal center exists at a position which will provide a catalyst which is effective to functionalize a primary C—H hydrocarbon bond.

Suitable transition metals a) (or M) include transition metals in the +1, +2, +3, +4, +5, or +6 oxidation state. It is preferred to employ a transition metal that is capable of traversing 2 or more formal oxidation states, more preferably 4 or more formal oxidation states. Accordingly, it is preferred to employ a metal having a formal oxidation state prior to bonding with the b) compound and the c) ligand(s) of +4, +5, or +6. Examples of suitable transition metals include Fe, Co, Ni, Rh, Ru, Os, Pt, Pd, Mn, Re, W, Cr, Mo, Ir, and the metals from the lanthanide and actinide series. Preferred metals are Re, Rh, and Ir. More preferred are Rh and Ir, and most preferred is Rh to improve the reaction rate over Ir and to improve the conversion of the functionalizing reagent to the hydrocarbon-functionalizing reagent adduct and other byproducts. It is generally believed that Ir transition metal centers promote faster reaction rates and are more completely convert C—H bonds than Rh using equivalent ligands and reaction conditions. Surprisingly, however, we have found that the reaction rate using Rh as a transition metal center to convert the functionalizing reagent to the functionalized hydrocarbon was faster and more complete than its Ir counterpart. Accordingly, in a most preferred embodiment, the transition metal is Rh.

The catalyst used in the process of the invention also comprises a source of a 3 to 8, cyclic or non-cyclic, aromatic or non-aromatic, neutral, cationic or anionic, substituted or unsubstituted electron donor moiety which does not dissociate under thermal reaction conditions, wherein said moiety
  (i) lacks aromatic C—H bonds on the moiety directly bonded to the transition metal, or
  (ii) contains sterically hindered aromatic C—H bonds on the moiety directly bonded to the transition metal;

The Z moiety depicted in the structural diagrams above (corresponding to the b) moiety) is a 3–8 electron donor ligand which does not dissociate under thermal reaction conditions. Thermal reaction conditions are all the physical reaction conditions employed in practice to functionalize the hydrocarbon at its primary C—H site, including but not limited to the pressure, temperature, space velocity, etc. conditions within the reaction vessel. Dissociation of the Z moiety results in the degradation of the catalyst, thereby terminating its activity.

The Z moiety also donates electron density to stabilize the oxidation state of the transition metal of the active catalyst. Preferably, the electronic charge of the Z moiety will fully stabilize the metal center depending upon the oxidation state of the metal center M in its active state.

The Z moiety may be between an $\eta^2$ and an $\eta^8$ complexed cyclic or non-cyclic, aromatic or non-aromatic, neutral cationic or anionic, substituted or unsubstituted ligand. It is preferably a π coordinated, cyclic aromatic compound fully substituted, and more preferably a cyclic, fully substituted aromatic, anionic moiety. In one embodiment, the Z compound is a fully substituted cyclic $\eta^5$ 5–8 carbon membered ring.

The Z moiety may be coordinated to the M metal center in several different isomeric configurations. For example, the Z moiety in the $\eta^5$ configuration may be in one of the S, W, or U isomeric states. In a more preferred embodiment, the Z moiety is the U isomer in the $\eta^5$ bonded configuration. It is to be understood that the original position of the double bonds of a dienyl ligand need not be identified because of the delocalization effect. For example, an $\eta^5$-1,3-pentadien-3-yl group is identical to the $\eta^5$-1,4-pentadien-3-yl group. It is to be further understood that all isomeric forms of Z moieties are included in any reference to a Z moiety identified herein. Furthermore, it is not critical to the invention that either the nature of the linkage between the Z moiety and the metal center, or the carbon number to which the Z moiety is coordinated, bonded, or completed to the metal center, be known, so long as some form of a linkage between the Z moiety and the metal center exists at a position which will provide a functionalizing reagent which is effective to functionalize a terminal C—H bond.

The Z moiety must lack aromatic C—H bonds on the moiety directly bonded to the transition metal, or contain sterically hindered aromatic C—H bonds on the moiety directly bonded to the transition metal. An aromatic C—H bond is a bond between a hydrogen atom and one of the carbon atoms forming the aromatic ring. The presence of sterically accessible aromatic C—H bonds on the moiety which will directly bond to the transition metal a) is undesirable because they compete with the functionalization of the primary C—H hydrocarbon bonds, thereby reducing the yield of functionalized hydrocarbon. Accordingly, the Z moiety should either altogether lack aromatic C—H bonds on the moiety directly bonded to the transition metal, or if such aromatic C—H bonds are present, they should be sterically inaccessible by other activated catalyst molecules in the vicinity to minimize or avoid functionalizing the Z moiety aromatic C—H sites.

In a more preferred embodiment, every site on the Z moiety, including those sites which are directly and only indirectly bonded to the transition metal through a substituent on the Z moiety directly bonded to the transition metal, are either lacking in any aromatic C—H bonds or contain sterically hindered C—H sites.

It will be appreciated that suitable substituents are bulky groups which are generally regarded as sterically demanding. Non-limiting examples of such bulky substituents on aromatic ring carbon atoms adjacent to the aromatic C—H site include hydrocarbyl, hydrocarbyl substituted metalloid radicals wherein the metalloid is selected from Group IV A or the Periodic Table, silyl, germyl, cyano, hydroxyl, amino, and halo groups, such as fluorine or chlorine, especially fluoro or fluoroalkyl groups, aryl, phenyl which optionally may bear one or more of the same or different substituents, alklaryl, alkoxy, phenoxy, phenylalkoxy, benzyl, bulky substituents containing one or more hetero atoms such as tri (loweralkyl)silyl, —NPh2, —NHPh, —BPh2, and —B(OPh)2, wherein n may be an integer of from 0 to 4, preferably from 0 to 2 and more preferably from 0 to 1, and m may be an integer of from 0 to 3, preferably from 0 to 2 and more preferably from 0 to 1, and carboxylic acid esters.

Any of the Z moiety substituents may be joined together on the Z moiety to form a $C_4$–$C_{20}$ saturated ring. Examples of hydrocarbyl groups include $C_1$–$C_{20}$ branched or unbranched alkyl groups, preferably $C_1$–$C_6$ branched or unbranched alkyl groups such as methyl, ethyl, isopropyl, propyl, butyl, t-butyl, isobutyl, neopentyl, and 3-phenyl-neopentyl. Other examples of hydrocarbyl groups include the $C_1$–$C_{20}$ substituted radicals, optionally where one or more of the hydrogen atoms may be replaced with a halogen radical, an amido radical, a phosphino radical, and an alkoxy radical or any other radical containing a Lewis acidic or basic functionality.

It is preferred that the subsitituent donate electron density to the ligand. Such substituents generally contribute to increasing the thermal stability of the catalyst under reaction conditions with the hydrocarbon, as well as increasing the activity of the catalyst.

Examples of preferred substituents comprise trimethylsilyl and $C_1$–$C_4$ branched or unbranched alkyl groups, such as methyl, isopropyl, t-butyl,.

The number of substituents is sufficient to create a fully substituted Z moiety or sufficiently substituted to sterically protect the remaining aromatic C—H bonds. The aromatic carbon atoms which are substituted include those carbon atoms in aromatic nuclei fused to an aromatic ring bonded directly to the metal center M, as well as the aromatic nuclei indirectly tethered to the transition metal through the non-dissociating electron donating atoms directly bonded to the transition metal.

Examples of b) moieties (equivalent to the Z moeities) include, but are not limited to, methylcyclopentadiene, ethylcyclopentadiene, t-butylcyclopentadiene, hexylcyclopentadiene, octylcyclopentadiene, 1,2-dimethylcyclopentadiene, 1,3-dimethylcyclopentadiene, 2,4-dimethyl-$\eta^5$-pentadien-1-yl, 1,5-dimethyl-$\eta^5$-pentadien-2-yl, 2,4-dimethyl-$\eta^5$-pentadien-3-yl, 1,5-dimethyl-5-pentadien-3-yl, 1,2,4-trimethylcyclopentadiene, pentamethylcyclopentadiene, 1, 5-bis(trimethylsilyl)-$\eta^5$-pentadien-3-yl, 1,2,3,4-tetramethylcyclopentadiene, 1,2,6,6-tetramethyl-5-cyclohexadien-4-yl, 1,2,4,6,6-pentamethyl-$\eta^5$-cyclohexadien-3-yl, 1,2,4,6,6-pentamethyl-$\eta^5$-cyclohexadien-5-yl, 1,2,5,6,6-pentamethyl-$\eta^5$-cyclohexadien-4-yl, 1,2,4,5,6,6-hexamethyl-$\eta^5$-cyclohexadien-3-yl; 1,2,4,5-tetramethyl-6,6-cyclotrimethylene-$\eta^5$-cyclohexadien-3-yl; 1,2-dihydronaphthalen-1-yl; 1,2-dihydronaphthalen-2-yl; 1,1-dimethyl-1,2-dihydronaphthalen-2-yl; 1,1-dimethyl-1,2-dihydronaphthalen-4-yl; diphenylmethyl-di(1-cyclohexenyl)methyl; 1,1-dimethyl-1,2,5,6,7,8-hexahydronaphthalen-4-yl; 1,1-dimethyl-1,4,5,6,7,8-hexahydronaphthalen-4-yl; 1,1-dimethyl-1,5,6,7,8,9-hexahydronaphthalen-4-yl; 1,1,2,3-tetramethyl-1,2,5,6,7,8-hexahydronaphthalen-4-yl; 1,1,2,3-tetramethyl-1,4,5,6,7,8-hexahydronaphthalen-4-yl; 1,1,2,3-tetramethyl-1,5,6,7,8,9- hexahydronaphthalen-4-yl; 9,10-dihydroanthracen-9-yl; 9,10-dihydroanthracen-1-yl; 9,9-dimethyl-9,10-dihydroanthracen-10-yl; 1,2,3,4,9,10-hexahydroanthracen-9-yl; 1,2,3,4,9,10-hexahydroanthracen-1-yl; 1,2,3,4,9,11-hexahydroanthracen-9-yl; 1,4,5,8,9,10-hexahydroanthracen-1-yl; 9,9-dimethyl-1,4,5,8,9,10-hexahydroanthracen-10-yl; 9,9-dimethyl-1,4,5,8,9,10-hexahydroanthracen-2-yl; 8,8-dimethyl-1,4,5,8,9,10-hexahydroanthracen-10-yl; 1,2,3,4,5,6,7,8,9,10-decahydroanthracen-9-yl; 1,2,3,4,5,6,7,8,9,11-decahydroanthracen-9-yl; 9,9-dimethyl-1,2,3,4,5,6,7,8,9,10-decahydroanthracen-10-yl; 9,9-dimethyl-1,2,3,4,5,6,7,8,9,11-decahydroanthracen-10-yl, 4,7-dimethylindene, 4,5,6,7-tetrahydroindene; 3-methylcyclopentadienylsilane, 1,2-dimethylcyclopentadienylsilane, 1,3-dimethylcyclopentadienylsilane, 1,2,4-trimethylcyclopentadienylsilane, 1,2,3,4-tetramethylcyclopentadienylsilane, pentamethylcyclopentadienylsilane, 1,2,4-trimethylindenylsilane, 1,2,3,4-tetramethylindenylsilane and pentamethylindenylsilane and each of their equivalent ligands. Other Z moieties include the fully substituted or sterically hindered substituted moieties of the compounds identified in U.S. Pat. No. 5,541,349 as the L ligand therein, which disclosure is fully incorporated herein by reference.

When Z is cyclic, the ring may optionally be comprised of heteroatoms, such as nitrogen or oxygen. Z can be a 4–50 member non-hydrogen atom group, preferably a 4–10 membered fully substituted cyclic moiety or a sterically hindered moiety comprised of a single or fused ring system. Examples of any of the above compounds bonded through an alkylene group (usually 2 to 8, preferably 2 to 3, carbon atoms) are suitable as the Z moiety. Examples of such compounds include bis(4,5,6,7-tetrahydro-1-indenyl)ethane, 1,3-propanedinylbisindene, 1,3-propanedinylbis(4,5,6,7-tetrahydro)indene, propylenebis(1-indene), isopropyl(1-indenyl)cyclopentadiene, diphenylmethylene(9-fluorenyl)cyclopentadiene, isopropylcyclopentadienyl-1-fluoreneisopropylbiscyclopentadiene. A mixture of any of the aforementioned compounds may be used in the synthesis of the catalyst.

Most preferred as the Z moieties are alkyl substituted cyclopentadienyl compounds, and in particular the $C_1$–$C_4$ alkyl substituted cyclopentadienyl compounds such as the mono, tri, tetra, or penta methyl, ethyl, propyl, isopropyl, or t-butyl cyclopentadienyl compounds (e.g. dimethylcyclopentadienyl, methylcyclopentadienyl, tetramethylcyclopentadienyl, diethylcyclopentadienyl, t-butylcyclopentadienyl, and pentamethylcyclopentadienyl) and the hydroxy and $C_1$–$C_4$ alkyl substituted indenyl and fluorenyl compounds, such as tetramethylindenyl, tetrahydrofluorenyl, and octahydrofluorenyl.

Some examples of cyclic Z moiety structures are represented below:

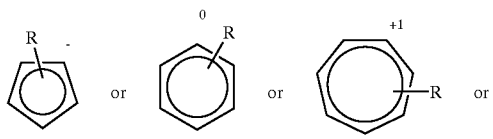

-continued

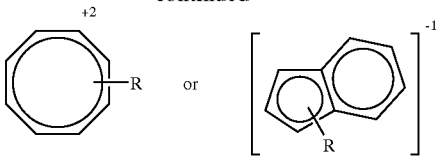

wherein Z is fully substituted with R groups or sufficient numbers of R groups to sterically hinder the aromatic C—H bonds. The number of R groups may range from 1 to 8.

The catalyst used in the process of the invention is also comprised of one or more c) ligands. The catalyst contains at least 1 c) ligand, and preferably contains 2 or more c) ligands. The c) ligand is derived from a source of ligands capable of formally donating an electron pair to the transition metal a) and which dissociate thermally.

The c) ligand is derived from sources which donate electron density to the transition metal and which contain either a non-bonding pair of electrons or a bonding pair of electrons. By "donating" a pair of electrons is meant that the ligand does not transfer electrons to the metal, and upon dissociation, the electrons leave with the ligand. It is not necessary that the bond linkage occur between a coordinating atom and the metal center. The bond linkage may occur between the metal center and a π bond or a π coordinated ring, each of which can donate electron density to stabilize the oxidation state of the metal center M, or the bond linkage may be a σ bond between a ligand atom and the transition metal center.

The c) ligand should be one which dissociates from the catalyst upon application of thermal energy. Since it is desirable to both increase product yield and reaction rates, not all of the ligands should be of the type which are tightly held to the transition metal center, and not all ligands should dissociate from the catalyst slowly or only at temperatures approaching the decomposition temperature of the catalyst. Accordingly, at least one of the ligands should thermally dissociate from the catalyst. By thermally dissociating is meant that the ligand is capable of dissociating from the metal center using thermal energy at temperatures below the temperature at which the b) moiety dissociates from the metal center, which would result in the degradation of the catalyst. In a preferred embodiment, the c) ligand dissociates from the metal center a) at temperatures below 250° C. and above 70° C. Evidence of thermal dissociation is to conduct the reaction in a dark room and in the absence of any co-catalyst or other ingredients beside the functionalizing reagent, the catalyst, the hydrocarbon, and a solvent.

The c) ligand can be broadly represented by the following structural formulas:

wherein X and Y each independently represent one or more of H, C, B, S, N, Si, Sn, P, and As and combinations thereof, to which saturated or unsaturated, branched or unbranched alkyl, aromatic, alicyclic, or alkaryl groups may be bonded, and wherein X and Y may be bridged to form a cyclic arene compound which may contain branches, substituents, or fused aromatic rings, R represents one or more optional branches or substituents, and n represents an integer ranging from 0 to 8. The unsaturation between X and Y may be olefinic or acetylenic. However, X and Y may also be bound by a single covalent bond when X or Y is hydrogen.

An example of a fused X—Y structure is represented by a 6 membered aromatic ring as shown in the structure below:

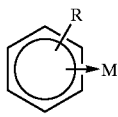

Preferred c) ligands satisfying the above criteria are derived from a source of :PR$_3$, :NR'$_3$, HSiR$_3$, unsaturated aliphatic compounds, π allyl, and π arene compounds. More preferred c) ligands comprise a source of HSiR$_3$, unsaturated aliphatic compounds, π allyl and π arene compounds. Most preferred are the unsaturated aliphatic compounds, π allyl compounds, and the π arene compounds, and especially the unsaturated aliphatic compounds and the π arene compounds.

Tertiary phosphines suitable as the c) ligand include the mono and bisphosphines. Monophosphines are represented by the formula:

:PR$_3$ wherein R is independently an aromatic of up to 14 carbon atoms, optionally substituted; or a C$_1$–C$_{40}$ alkyl or alicyclic group, optionally containing atoms other than carbon and hydrogen in the form of monovalent substituents which are preferably electron-withdrawing substituents such as halo, preferably the middle halogens chloro and bromo, nitro and trifluoromethyl. Examples of aromatic R' groups include phenyl, tolyl and naphthyl. The aromatic groups are optionally substituted aryl groups with halogen atoms and alkyl, aryl, alkoxy, carboxy, carbalkoxy, acyl, trihalogenmethyl, cyano, dialkylamino, sulphonylalkyl and alkanoyloxy groups.

Other specific examples of suitable phosphines are bis(1, 1-dimethylethyl) phenylphosphine, dimethylphenylphosphine, cyclohexyldiphenylphosphine, dibutylphenylphosphine, methyldiphenylphosphine, triphenylphosphine, tri-n-butylphosphine, tris(4-tolylphosphine), tris(4-chlorophenyl)phosphine, tris(4-methoxyphenyl)phosphine, tris(3-methoxyphenyl) phosphine, tris(2-methoxyphenyl)phosphine, tris(4-butylphenyl)phosphine, tris(4-triflurophenyl)phosphine, tris (4-fluorophenyl)phosphine and 2-carboxyphenyl diphenylphosphine, tri-p-tolylphosphine, tri-p-methoxyphenylphosphine, o-diphenylphosphinobenzoic acid, and in particular triphenylposphine, tributylphosphine, trimethylphosphine, triethylphosphine, tripropylphosphine, and any C$_1$–C$_6$ alkyl combination as an R' group, 1,2-bis (diphenyl-phosphino) ethane, 1,2-bis(diphenylphosphino) ethene, 1,3-bis (diphenylphosphino) propane, 1,3-bis (diethylphosphino) propane, 1,4-bis (diphenylphosphino) butane, 1,3-bis(di-isopropylphosphino) propane and 1,3-bis (di-p-methoxyphenyl phosphino) propane.

Tertiary amines suitable as the c) ligand are represented by the formula:

:NR'$_3$ wherein R' has the same meaning as R above with respect to :PR$_3$, as well as the polyamines such as the diamines, triamine, and pentamines.

Examples of electron donating c) amine ligands include trimethylamine, triethylamine, tri-n-propylamine,. triisopropylamine,tri(n-butyl)amine, tri(isobutyl)amine, N,N-dimethylaniline, tributylamine,benzyldimethylamine, tris(dimethylaminomethyl)phenol, dimethylethanolamine, n-methylmorpholine, triethylene diamine, N-methylmorpholine,N-ethylmorpholine, diethyl-ethanolamine, N-cocomorpholine,1-methyl-4-dimethyl-aminoethylpiperazine, 3-methoxypropyldimethylamine,N,N,N'-tri-methylisopropyl propylenediamine, 3-diethylamino propyl-diethylamine,dimethylbenzylamine, dimethylcyclohexylamine, 2-methylimidazole, 2-phenylimidazole,2-ethyl-4-methyl imidazole, 2,4,6-tris (dimethylaminomethyl)phenol, 1,4-diazabicyclo(2,2,2)-octane, 1,5-diazabicyclo(5,4,0)-undecane, dimethyldodecylamine, pyridine, 4-(1-butylpentyl)pyridine, quinoline, isoquinoline, lipdine, quinaldine, nonylpyridine, 2,6-lutidine, 2,4,6-collidine, 2-undecylimidazole, 2-heptadecylimidazole, 2-phenylimidazole,2-ethyl-4-methylimidazole,1-benzyl- 2-methylimidazole,l-propyl-2-methylimidazole, 1-cyanoethyl-2-methylimidazole,l-cyanoethyl-2-ethyl-4-methylimidazole, 1-cyanoethyl-2-undecylimidazole,1-cyanoethyl-2-phenylimidazole, 1-guanaminoethyl-2-methylimidazole, N,N-dimethylaniline, N,N-dimethyltoluidine, N,N-dimethyl-p-anisidine, p-halogeno-N,N-dimethyl-aniline, 2-N-ethylanilino ethanol, tri-n-butylamine, pyridine, quinoline, N-methylmorpholine, triethanolamine, and N,N,N',N'-tetramethylbutanediamine.

The source of unsaturated aliphatic compounds as the c) ligand must contain C and H, although heteroatoms may also be present in the compound, provided that not more than 1 heteroatom for every 6 carbon atoms are present. Any aliphatic compound containing unsaturation which dissociates from the transition metal center at a temperature lower than the temperature at which the b) moiety (Z group) dissociates, is a suitable compound for use as a ligand.

The aliphatic unsaturated compound may have from 2 to 32 carbon atoms, preferably from 2 to 8 carbon atoms, more preferably from 2 to 6 carbon atoms. The aliphatic unsaturated compound may be alicyclic or in a linear or branched non-ring structure. Mono- or poly- olefins straight or branched chain compounds are preferred, with mon-olefins being more preferred.

Suitable unsaturated aliphatic compounds as the c) ligand include mono-olefins such as the linear olefins made by the cracking of paraffin wax, commercial olefin products manufactured by ethylene oligomerization are marketed in the United States by Shell Chemical Company under the trademark NEODENE, linear internal olefins made by the chlorination-dehydrochlorination of paraffins, by paraffin dehydrogenation, and by isomerization of alpha-olefins, detergent-range internal or alpha, branched or unbranched, mono-olefins containing from about 8 to about 22 carbon atoms such as those in the carbon number range of C10 to C12, C11 to C15, C12 to C13, and C15 to C18, and ethylene, propylene, 1-butene, 2-butene, 1-pentene, 2-pentene, isopentene, hexene-1, 2-hexene, 3-hexene, 4-methylpentene-1, 2-methylpentene-1, 4-methylbutene-1, 1-heptene, 2-heptene, 3-heptene, 1-octene, 2-octene, 2-methylheptene-1, 4-octene, 3,4-dimethyl-3-hexene, 1-decene, and 1-dodecene, and so forth up to 32 carbon atoms ; dienes and trienes including butadiene, 1,3-pentadiene, 1,4-pentadiene, 1,3-hexadiene, 1,4-hexadiene, 1,5-hexadiene, 1,3-cyclohexadiene, 1,4-cyclohexadiene, 1,9-decadiene 1,13-tetradecadiene, 2,6-dimethyl-1,5-heptadiene, 2-methyl-2,7-octadiene, 2,7-dimethyl-2,6-octadiene, 2,3-dimethylbutadiene, ethylidene norbornene, dicyclopentadiene, isoprene, 1,3,7-octaroriene, 1,5,9- decartriene, 4-vinylcyclohexene, vinylcyclohexane; divinylbenzene, and cyclic olefins including cyclopentene, cyclobutene, cyclohexene, 3-methylcyclohexene, cyclooctene, cyclodecene, cyclododecene, η5-cyclohexadienyl, η6-cycloheptatriene, η8-cyclooctatetracene tetracyclodecene, octacyclodecene, norbornene, 5-methyl-2-norbornene, 5-ethyl-2-norbornene, 5-isobutyl-2-norbornene, 5,6-dimethyl-2-norbornene, 5,5,6-trimethyl-2-norbornene; and acetylenic compounds such as acetylene, methylacetylene, diacetylene, 1,2-dimethylacetylene, eta 3-pentenyl, and norbornadiene.

Sources of the π allyl compound may contain from 3 to 64 carbon atoms. The electronic configuration of the π allyl is not particularly limited, but will generally take on the $\eta^3$ state. Any π allyl which dissociates from the transition metal center at a temperature lower than the temperature at which the b) moiety (Z group) dissociates, is a suitable compound for use as a ligand.

Specific examples of π allyl compounds include allyl acrylate, 2-propen-1-ol, allylamine, allylbromide, allyl hexanoate, allyl cyanide, allyl carbonate, 1-allyl-4-hydroxybenzene, allyl-alpha-ionone, allyl isocyanate, allyl isothiocyanate, allyl thiol, allyl methacrylate, 4-allyl-2-methoxyphenol, 4-allyl-1,2-methylenedioxybenzene, allyl pelargonate, allyl sulfide, and allyl thioureas.

The π-arene compound may contain from 5 to 64 carbon atoms, preferably from 5 to 14 carbon atoms. The electronic configuration of the π allyl and the n-arene compound is not particularly limited, and may take on the $\eta^3$, $\eta^4$, $\eta^5$, $\eta^6$, $\eta^7$, and $\eta^8$ states, and may also have any isomeric structure within each η configuration, including the W, U, and S configurations. Any π arene compound, whether substituted, fused, or bridged, which dissociates from the transition metal center at a temperature lower than the temperature at which the b) moiety (Z group) dissociates, and which lacks aromatic C—H bonds on the moiety directly bonded to the transition metal, or contains sterically hindered C—H bonds on the moiety directly bonded to the transition metal, is a suitable compound for use as a ligand. Reference can be had to the Z moiety substituents described above to determine suitable substituents to sterically hinder the presence of aromatic C—H bonds on the c) ligand.

Suitable π arenes as the c) ligand include divinylbenzene, p-xylene, 1,3,5-trimethylbenzene (mesitylene), 1,2,4-trimethylbenzene, 1,3,5-triisopylbenzene, 1,2,3,4-tetramethylbenzene, 1,2,3,5-tetramethylbenzene, 1,2,4,5-tetramethylbenzene (durene), pentamethylbenzene, hexamethylbenzene, fluorene, dibenzostannepine, tellurophene, phenothiarsine, selenanthrene, phenoxaphosphine, phenarsazine, phenatellurazine, 1,2,3,4,4a,9a)-9-(phenylmethylidene)fluorene, and (1,2,3,4,4a,9a)-9-(3-phenyl-2-propenylidene)fluorene.

The source of c) ligand may also comprise compounds derived from polyalkylsilanes. Such silanes can be represented by the following formula:

wherein R" is hydrogen, or has the same meaning as R above with respect to suitable phosphine compounds as the c) ligand, and n is an integer ranging from 3–4, provided that the silane contains no more than two hydrogen atoms bonded to the silicon atom.

Most preferred examples of the c) ligand are represented by the following structural formulas:

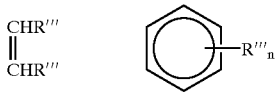

wherein each R'" independently represents hydrogen or a saturated or unsaturated, branched or unbranched alkyl, aromatic, alicyclic, or alkaryl group having from 1 to 15 carbon atoms or one or more fused ring structures, more preferably hydrogen or a saturated, branched or unbranched alkyl group having from 1 to 8 carbon atoms, most preferably from 1 to 4 carbon atoms; and n represents the number of R'" groups and is an integer ranging from 2 to 6. The electronic configuration of the aromatic radical may be in the $\eta^4$, $\eta^5$, or $\eta^6$ states.

Examples of these most preferred c) ligands include ethylene, propylene, 1-butene, 2-butene, 2-methyl-propene-1, 1,4-di-t-butylbenzene, 1,3,5-trimethylbenzene (mesitylene), 1,2,4-trimethylbenzene, 1,3,5-triisopylbenzene, 1,2,3,4-tetramethylbenzene, 1,2,3,5-tetramethylbenzene, 1,2,4,5-tetramethylbenzene (durene), pentamethylbenzene, hexamethylbenzene, and di-t-butylbenzene. Among these, ethylene and alkyl substituted $C_6$ compounds, such an tri-, tetra-, penta-, and hexa- $C_1$–$C_4$ alkyl substituted $C_6$ are particularly suitable.

While mention has been made of employing c) ligands, any other compound known to act as a ligand may be used in addition to the c)ligand. Examples of additional ligands which may be bonded to the transition metal center include hydrogen, CO, phosphite, alkoxy, amido, aryloxide, phosphido, arsenic radical, carbonates such as $CF_3CO_2^-$, sulfonates such as $CF_3SO_3^-$, and silyl groups.

The total sum of electrons donated by the ligands and the valence electrons possessed by the transition metal is governed by the "eighteen electron rule" in most cases. This rule states that the most stable organo-metallic compounds tend to be those compounds in which the sum of the electrons donated by the ligands and the metal is eighteen. Those skilled in the art, however, know that there are exceptions to this rule and that organometallic complex compounds having a sum of 16, 17, 19, and 20 electrons are also known. Therefore, organometallic catalysts described herein in which the complexed metal M have a total sum of 16, 17, 18, 19, or 20 electrons in the valence shell and a residual net positive charge of 1, 2 or 3 are included within the scope of the invention.

The catalyst may be synthesized by any of the known literature methods. The halide of the metal-Z moiety can be synthesized by the methods described in C. White, A. Yates, P. M. Maitlis, Inorg. Synth. 1992, V29, 228–234, incorporated herein fully by reference. The catalyst may be manufactured by combining in any sequence, but preferably by combining c) with the reaction product of a) and b).

Commercially available Z moiety -complexed metals, such as cyclopentadienyl metals, are generally complexed with a ligand other than an olefin or aromatic ligand. A typical ligand in commercially available cyclopentadienyl metal compounds is —CO. Any known method for substituting one ligand for another may be used to prepare the catalyst. The synthesis and purification of the catalyst including the ligands can be performed according to the methods described in T. M. Gilbert, R. G. Bergman, Inorg. Synth., 1990, V.27, 19–22; K. Moseley, J. W. Kang, P. M. Maitlis, J. Chem.Soc. A, 1970, 2875–83; W. J. Bowyer, J. W. Merkert, W. E. Geiger, Organometallics, 1989, V.8, 191–198; and C. White, P. M. Maitlis, J.Chem.Soc.A 1971, 3322–3326, each of which are incorporated herein fully by reference. In general, a molar ratio of Z-metal halide salt moieties to the c) ligand compound, as determined by the desired number of ligand compounds bonded to the transition metal, are mixed together in the presence of an optional solvent and acid under heat at −78° C. to 100° C. for a time sufficient to fully exchange the halide ligands with the c) ligands, after which the product is cooled and the acid removed by distillation under vacuum. The resulting solid may be washed with water and filtered. An aqueous source of a weakly coordinating anion such as $NH_4PF_6$ is mixed with the filtrate to precipitate the desired product, which may then be washed with more water and dried.

Examples of acids useful as agents to ionically bond the halide to the complex include $CF_3COOH$, RCOOH, $CF_3$—$SO_3H$, and other weakly coordinating acids. Examples of other anionic sources useful to precipitate the catalyst include $NH_4BF_6$, $NH_4AsF_6$, $NH_4OH$, $NBa_4PF_6$, and the like.

The process of the invention selectively functionalizes a hydrocarbon with functionalizing reagent. The functionalizing reagent comprises any group having an electropositive atom capable of bonding to the metal center M and making a strong E—C bond where E is the electropositive element. The overall reaction is between the reagent containing the electropositive element X—E and the carbon-hydrogen C—H converting to an X—H bond and a carbon-electropositive bond C—E, where X can be hydrogen, another electropositive atom, or other sacrificial portion of the molecule. The electropositive element should be chosen such that the absolute value of the C—H, X—E, C—E, and X—H bond energies satisfy the following equation:

C—H+X—E<C—E+X—H

Preferably, the functionalizing reagent comprises a source of boron. The source of -boron compounds include numerous boron alkyl, boron aryl, organoboron hydride, or organoboron halide compounds that are known and/or may be prepared in a known manner. The types of boron compounds and their methods of preparation are described in "Mechanism of the Complexation of Boron Acids with Catechol and Substituted Catechols" by Pizer, R. and Babcock, L., Inorganic Chemistry, vol. 16, No. 7 pp. 1677–1681 (1977); R. K. Boeckman et al. "Catechol boron halides: . . . " Tetrahedron Letter, 1985, 26, pp. 1411–1414; S. Pereira, M. Srebnik, Tetrahedron Lett. 1996, V37, 3283–3286; C. E. Tucker, J. Davidson, P. Knochel, J.Org.Chem., 1992, V.57, 3482; R. A. Bowie, O. C. Musgrave, J.Chem.Soc. 1963, 3945–3949; and Herbert C. Brown, "Organic Synthesis via Boranes", John Wiley & Sons, 1975, each incorporated herein fully by reference.

Typical representatives of suitable sources of boron compounds are polyalkylmonoboranes and diborane compounds or Lewis base adducts of diborane. Examples of monoboranes include sodium borohydride, potassium borohydride, lithium borohydride, sodium trimethylborohydride, potassium tripropoxy-borohydride, tetramethylammoniumborohydride, triphenylborane, sodium tetraphenylborate, lithium tetraphenylborate, sodium hydrido tris(1-pyrazol)borate, potassium dihydro bis(1-pyrazol)borate, lithium triethylborohydride, lithium tri-sec-butylborohydride, potassium tri-sec-butylborohydride, sodium cyanoborohydride, zinc borohydride, bis(triphenylphosphine) copper (I) borohydride, potassium tetraphenylborate, lithium phenyltriethylborate, lithium phenyltrimethoxyborate, sodium methoxytriphenylborate, sodium diethylaminotriphenylborate, and sodium hydroxytriphenylborate.

In general, boranes derived from olefin hydroboration are useful. These boranes can be triethylborane, dicyclohexylborane, dihexylborane, diethylborane, ethylborane, boron alkyls such as 9-bora-bicyclo-[3.3.1] nonane, diisopinocampheyl borane, dicyclohexyl borane, 2,3-dimethyl-2-butyl borane, 3,5-dimethylborinane and diisoamyl borane, diisopinocampheyl borane, thexylcyclohexyl borane, thexyllimonyl borane, and dinorbornylboron. Further suitable sources of mono-boranes are reaction products of 1,2-dihydroxybenzenes or 4,6-dimethyl, 1,2-dihydroxybenzenes with boron hydride (boryl catechol or boryl 4,6-dimethylcatechol) and tri-n-butyl boroxine. The boryl compounds in their halogenated state provide a synthetic route to making the functionalizing reagent. Boryl compounds may be reacted in their halo-form with the metal or organo-metallic compounds or complexes. An example of a type of haloboryl compound is the family of halocatecholborane, available commercially. Any halide is suitable, including Cl, Br, and I. The haloboryl compounds in this family may be prepared by reacting an $R(OH)_2$ compound with $BX_3$, where X is a halide.

Examples of structures for sources of haloboryl compounds are represented by the following formulas:

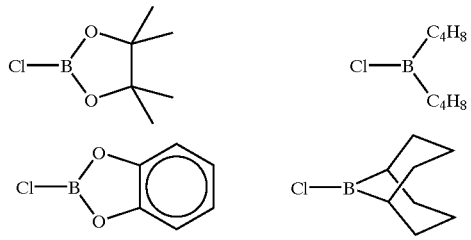

Bis(dioxaborolane) compounds may be conveniently prepared by reduction of halodiaminoboranes using sodium metal, and subsequent reaction with diols in the presence of acid.

Preferred boron containing functionalizing reagents are the branched or unbranched, substituted or unsubstituted pinacol derivatives of mono- or di-boron. Other examples of diboryl adducts include tetrakis dimethylaminodiboron, bis-catecholate diboron, and substituted bis-catecholate diboron. Preferred diboryl compounds contain a moiety represented by the following structural formula:

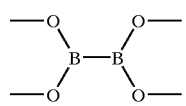

In another embodiment, a preferred diboryl functionalizing reagent is represented by the structure:

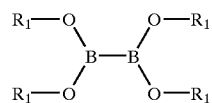

wherein each $R_1$ independently represents an alkyl group having from 1 to 24 carbon atoms, alkoxy groups contain from 3 to 24 carbon atoms, a cycloaliphatic group containing from 3 to 8 carbon atoms, or an aryl group containing from 5 to 16 atoms, and each of the alkyl, aryl, alkoxy, and cycloaliphatic groups in the aforementioned dioxaborolane compounds may be linear or branched; or substituted with halogens, such as fluorine or bromine, or alkyl groups having from 1 to 16 carbon atoms, preferably from 1 to 4 carbon atoms, and optionally each $R_1$ group attached to the same boron atom through oxygen atoms may be fused or bridged through any of the aforesaid alkyl, alkoxy, cycloaliphatic or aryl groups.

Examples of preferred bis(dioxaborolane) containing compounds include bis-pinacolate diboron and bis(t-butylcatecholate) diboron.

The hydrocarbon, preferably an alkane, is selectively functionalized at the primary C—H site by simply combining the catalyst, functionalizing reagent and hydrocarbon under functionalizing reaction conditions. To initiate the reaction by dissociating the ligand from the catalyst, the reaction mixture is heated to any temperature above the temperature at which the catalyst is stored, or room temperature, whichever is less, and below the thermal decomposition temperature of the catalyst or functionalizing reagent. It is desirable that the reagent species employed activates at temperatures above those the reagent would encounter during shipping or storage to ensure storage stability. Accordingly, suitable reaction temperatures range from 70° C. to about 250° C., more preferably from 100° C. to 200° C.

While the molar ratio of ingredients is not critical, it is desirable to use a stoichiometric excess of functionalizing reagent over the metal catalyst (>1:1), and preferably a molar ratio of >10:1, and more preferably >100:1, and most preferably >200:1, respectively. The amount of catalyst is also not particularly limited. However, an amount of catalyst ranging from 0.1 to 10 mole %, preferably from 0.1 to 5 mole %, based on the combined moles of catalyst and hydrocarbon will operate to functionalize the hydrocarbon at the primary C—H site. Other reaction conditions are not particularly limited.

The reaction time is not limited, other than the reaction time should be as short as possible to reduce. cycle time and increase throughput. Reaction times may range from 0.5 hours to 48 hours. The reaction may be carried out at any desired pressure. Pressures within the range of 0 p.s.i.g. to 100 p.s.i.g. are suitable. The reaction between the functionalizing reagent and the hydrocarbon in the presence of the catalyst may be carried out in any solvent for both the reagent and hydrocarbon. The process of the invention advantageously employs the hydrocarbon as the solvent for the functionalizing reagent without need to add additional solvent.

Once the reaction is complete, the functionalized hydrocarbon may be separated and isolated from the reaction mixture by distillation, chromatography, or crystallization.

The process of the invention is 80% or more selective toward functionalizing a primary C—H bond on hydrocarbon molecules, in contrast to a secondary C—H bonding site. Of the C—H sites on the hydrocarbon which are converted, the process of the invention is capable of selectively functionalizing 90% or more, preferably 95% or more, and more preferably 98% or more, and most preferably 99% or more of the converted C—H sites on the hydrocarbon at the primary C—H site.

The process is also catalytic. The process of the invention enables one to thermally activate the catalyst while achieving 50 or more turnovers. The number of catalyst turnovers is calculated by dividing the moles of product made by the moles of catalyst added to the process. Preferably, the catalyst turns over more than 75 times, more preferably 100 times or more.

Without being bound to a theory, and for illustration purposes only, it is believed that one possible mechanism for the functionalization of the hydrocarbon, using $B_2pin_2$ and a $Cp*Rh(C_2H_2)_2$ ($Cp*=\eta^5 C_5Me_5$) and nonane as illustrative examples of the functionalizing reagent, catalyst, and hydrocarbon, respectively, proceeds according to the following catalytic cycles:

First Stage: $B_2pin_2$ as reagent:

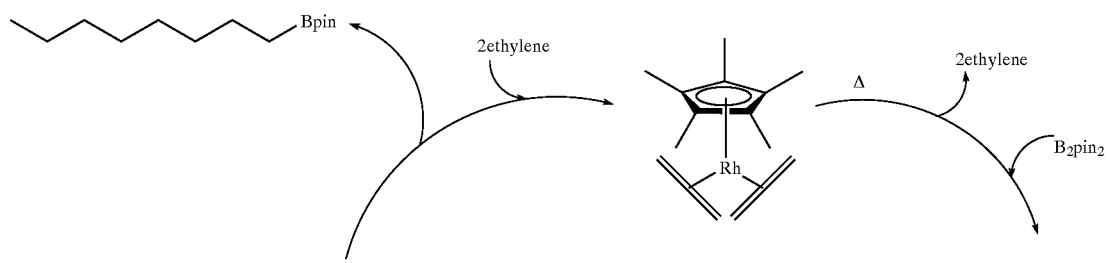

-continued

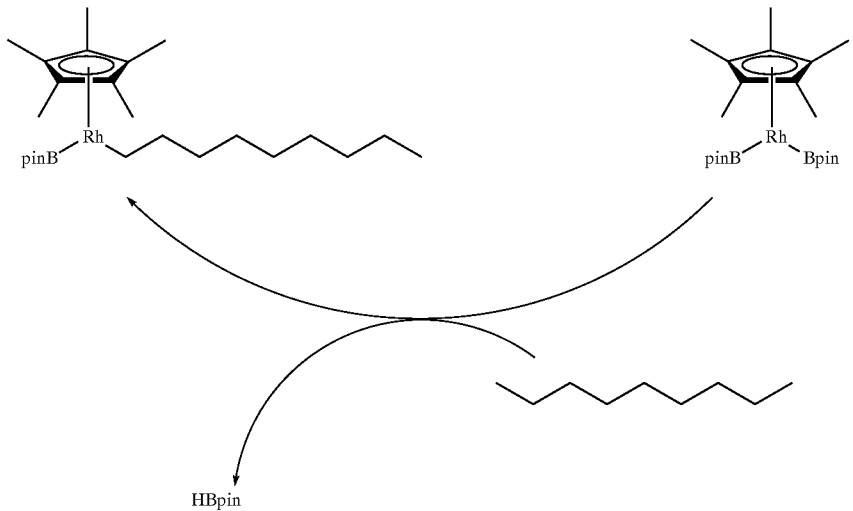

Second Stage: HBpin as reagent

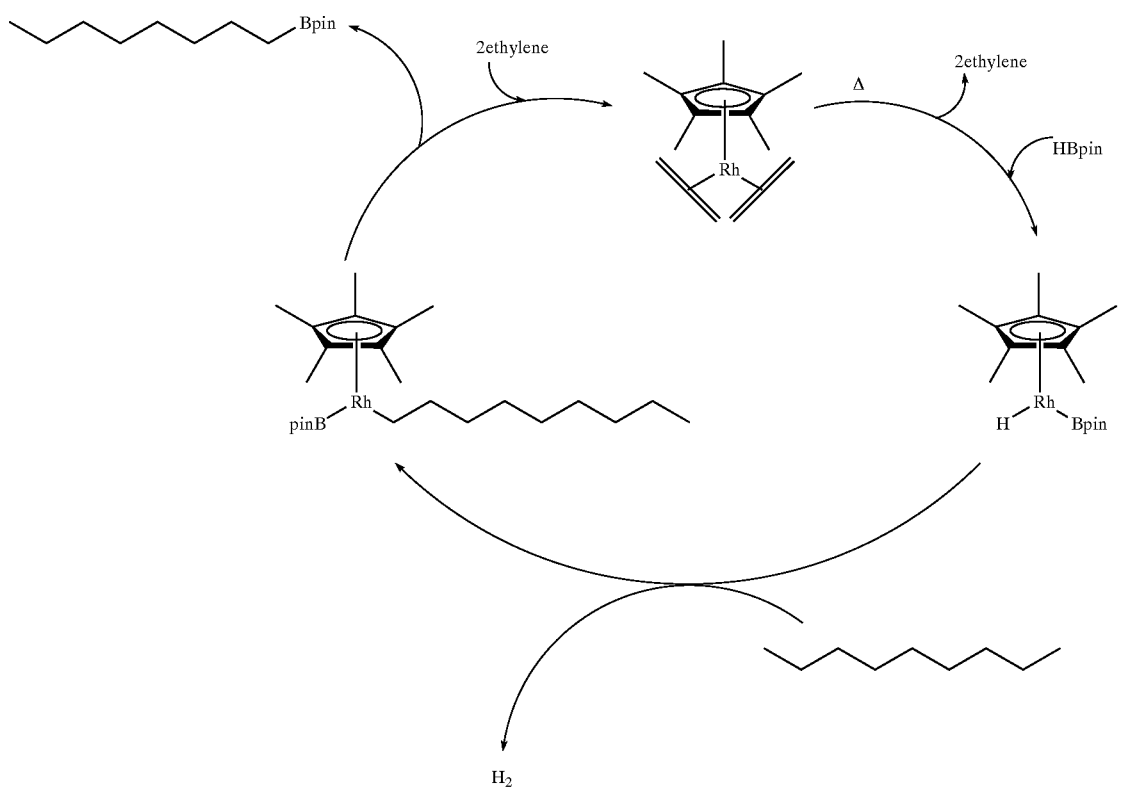

Once the hydrocarbon is functionalized as a boryl adduct of the hydrocarbon at a primary C—H site, the adduct may be converted into any other hydrocarbyl containing functional group using well known and conventional processes, such as those described in H. C. Brown, "Hydroboration," 1962; R. C. Larock, "Comprehensive Organic Transformations; A Guide To Functional Group Preparations," New York, N.Y., 1989; and H. C. Brown, "Organic Synthesis via Boranes," New York, N.Y., 1975. For example, primary alcohols can be manufactured by the oxidation of the primary alkylboryl adduct using an alkali metal hydroxide solution in the presence of a peroxide, or the adducts may be carbonylated to an alcohol by reacting the primary alkylboryl adduct in the presence of carbon monoxide, water and an alkali metal hydroxide such as NaOH or KOH.

Carboxylic acids can be prepared by oxidation of the borane functionalized hydrocarbon to an alcohol, followed by conventional oxidation of the alcohol to the acid. Amine functional hydrocarbons can be prepared by reaction of borane functionalized hydrocarbon with o-hydroxylamine sulfonic acid and chloroamine"

The functionalized borane hydrocarbons converted to —OH, —COOH, and —NH$_2$ or —NHR bearing compounds may be further converted to hydrocarbons containing ester, amide, imide, carbonate and polycarbonate, sulfonate, ether, polyether, and glycidyl ether groups.

EXAMPLES

Unless otherwise noted, all manipulations were carried out in an inert atmosphere glovebox or by using standard Schlenk line techniques. Solids were handled in a Vacuum Atmospheres drybox under nitrogen. All solvents were dried over appropriate reagents and distilled under nitrogen before use. $^1$H NMR and $^{13}$C NMR spectra were recorded on either a General Electric QE-300 or Bruker AM-500 NMR spectrometer, and $^{11}$B and $^{31}$P (H) NMR spectra were recorded on an Omega 300 NMR spectrometer. $^{11}$B and $^{31}$P(H) chemical shifts are reported in ppm relative to external standards of $BF_3$ $Et_2O$ and 85% $H_3PO_4$, respectively. Proton chemical shifts are reported in ppm relative to residual protiated solvent as internal standard. Elemental analysis were performed by Atlantic Microlabs, Inc., of Norcross, Ga. Octane, decan, methylcyclohexane and benzene were distilled from sodium/benzophenone ketyl prior to use. Benzene $D_6$ was dried over sodium/benzophenone ketyl and degassed before use. $B_2pin_2$ and HBpin were purchased from Frontier Science or Aldrich and were used as received. 1-Octene, 1-decene, ethylene, trimethylborate, triethylsilane, vinyltrimethylsilane, anhydrous n-butyl ether, and dodecahydrotriphenylene were purchased from Aldrich and were used as received without further purification. The metal compoundes $RhCl_3.3H_2O$ and $IrCl_3.H_2O$ were obtained from Johnson-Matthey.

$^{31}$P NMR was operating at 121 MHz, and $^1$H NMR was operating at 300 or 500 Hz. $^{11}$B NMR was operating at 96.4 MHz. All $^{31}$P NMR spectra were proton-decoupled. Integration of the $^{31}$P resonances were carried out on spectra that were acquired with gated decoupling and 10 second delay times between acquisition pulse sequences. $^1$H chemical shifts were measured relative to partially deuterated solvent peaks.

Catalyst Precursor Example 1

This example illustrates the synthesis of one embodiment of the catalyst precursor used to make a catalyst within the scope of the invention.

$[C_5Me_5RhCl_2]_2$ was synthesized according to the following procedure: A solution of 0.0042 moles of rhodium trichloride hydrate commercially available from Strem Chemicals and 0.007 moles of pentamethylecyclopentadiene commercially available from Aldrich in 40 ml methanol was refluxed under nitrogen for 48 hours with stirring. This procedure is described in C. White, A. Yates, P. M Matilis, Inorg.Synth. 29, 228–234 (1992), the contents of which are incorporated herein by reference. $[C_5Me_5RhCl_2]_2$ precipitated out of solution. It was collected and purified by recrystallization in a chloroform/hexane. The yield was 0.93 grams.

Catalyst Precursor Example 2

This example illustrates that synthesis of another embodiment of the catalyst precursor to make a catalyst within the scope of the invention.

$[C_5Me_5IrCl_2]_2$ was synthesized according to the following procedure: A solution of about 0.0058 moles of iridium trichloride hydrate commercially available from Strem Chemicals and 0.0085 moles of pentamethylcyclopentadiene commercially available from Aldrich in 40 ml methanol was refluxed under nitrogen for 48 hours with stirring. The $[C_5Me_5IrCl_2]_2$ product precipitated out of solution. It was collected and purified by recrystallization from chloroform/hexane. The yield was 1.05 grams.

Catalyst Example 3

This example illustrates that synthesis of another embodiment of the catalyst within the scope of the invention.

$C_5Me_5IrH_4$ was synthesized according to the following procedure: Air stable $[Ir(C_5Me_5)]_2(M—H)_3[PF_6]$, wherein M is the bridging ligand, was prepared by bubbling hydrogen gas through a solution of 0.000834 moles of $[C_5Me_5IrCl_2]_2$ in a mixture of 2-propanol, acetone, and water in a volume ratio of 2:2:1. The resulting $[Ir(C_5Me_5)]_2(NH)_3[PF_6]$ product was isolated by filtration, evaporation of acetone and isopropanol and treatment with a an aqueous solution of 0.001 mol $NH_4PF_6$ in 3 mL of water. $[Ir(C_5Me_5)]_2(NH)_3[PF_6]$ was collected by filtration and purified by crystallization from $CHCl_3$ and heptane. 200 mg, or 0.249 mmoles of the $[Ir(C_5Me_5)]_2(NH)_3[PF_6]$ product was slurried in hexane, cooled to about −40° C., after which a 1.5 mmol of $Li[BEt_3H]$ in 2 mL of toluene was added by pipette to the cooled slurry in a inert atmosphere glovebox. The resulting $C_5Me_5IrH_4$ product was isolated by filtering the slurry through an alumina column, followed by removal of the solvent through by evaporation under vacuum. 128 mg of the crude catalyst product was purified by sublimation at 30–40° C. and 20 mtorr. The procedure for synthesis of this catalyst is also explained in Gilbert, R. G. Bergman, Inorg. Synth. 27, 19–22 (1990).

The yield of the $(\eta^5C_5Me_5)IrH_4$ catalyst product was 36% (59 mg., 0.18 mmol). The spectroscopic characterization was as follows: $^1$HNMR ($C_6D_6$): δ1.99 (s, 15H), −15.4 (s. 4H).

Catalyst Example 4

This example illustrates that synthesis of another embodiment of the catalyst within the scope of the invention.

$C_5Me5Ir(ethylene)_2$ was synthesized according to the following procedure: Ethylene was bubbled into a suspension of 240 mg, or 0.301 mmol, of $[C5Me_5IrCl_2]_2$ in anhydrous sodium carbonate in ethanol under a nitrogen pad at 70° C. for 3 hours. The crude procts was obtained by filtration and the removal of the solvent by evaporation. The crude catalyst was sublimed at 25° C. at 5 mtorr to purify. The procedure for the synthesis of this catalyst is described in K. Moseley, J. W. Kang, P. M. Matilis, J. Chem. Soc A, 2875–83 (1970), the contents of which are incorporated herein by reference.

The yield of the $C_5Me_5Ir(ethylene)_2$ catalyst product was 82%(189mg., 0.492 mmol). The spectroscopic characterization was as follows: $^1$HNMR ($C_6D_6$): δ1.78 (m, 4H), 1.56 (s. 15H), 1.14 (m, 4H).

Catalyst Example 5

This example illustrates that synthesis of another embodiment of the catalyst within the scope of the invention.

$C_5Me_5Rh(ethylene)_2$ was synthesized according to the following procedure: Ethylene was bubbled into a suspension of 240 mg, or 0.324 mmol, of $[C_5Me_5RhCl_2]_2$ in anhydrous sodium carbonate in ethanol under a nitrogen pad at 70° C. for 3 hours. The crude products was obtained by filtration and the removal of the solvent by evaporation. The crude catalyst was sublimed at 25° C. at 5 mtorr to purify. The procedure for the synthesis of this catalyst is described in K. Moseley, J. W. Kang, P. M. Matilis, J. Chem. Soc A, 2875–83 (1970), the contents of which are incorporated herein by reference.

The yield of the $\eta^5$-$C_5Me_5$Rh(ethylene)$_2$ catalyst product was 410 (79mg., 0.267 mmol). The spectroscopic characterization was as follows: $^1$HNMR ($C_6D_6$): δ1.96 (m, 4H), 1.58 (s. 15H), 1.51 (m, 4H).

Catalyst Example 6

This example illustrates that synthesis of another embodiment of the catalyst within the scope of the invention.

$C_5Me_5Rh(C_2H_3SiMe_3)_2$ was synthesized according to the following procedure: $[C_5Me_5IrCl_2]_2$ was reduced by zinc powder 411 mg in the presence of 489 mg, 4.8 mmol, vinyltrimethylsilane in a solution of tetrhydrofuran at 20° C. for 12 hours. The product obtained was isolated by filtration and the removal of solvents by evaporation. The procedure for the synthesis of this catalyst is described in K. Moseley, J. W. Kang, P. M. Matilis, J. Chem. Soc A, 2875–83 (1970), the contents of which are incorporated herein by reference.

The yield of the $[C_5Me_5Rh(C_2H_3SiMe_3)_2$ catalyst product was 82%(143 mg.,0.326 mmol). The spectroscopic characterization was as follows: $^1$HNMR ($C_6D_6$): δ2.2 (dd, J=11.0, 2.3 2H), (s. 15H), 1.50 (s, 15H), 1.22 (m, 4H), 0.28 (s, 18H).

Catalyst 7

This example illustrates that synthesis of another catalyst.

$\eta^5$-$C_5Me_5RhH_2(SiEt_3)_2$ was synthesized according to the following procedure: 167 mg, 0.210 mmol of $[C_5Me_5RhCl_2]_2$ was combined with 820 mg., 7.05 mmol, triethylsilane under stirring in dry toluene for 8 hours at 60° C. and then 3 days at 20° C. The crude product was isolated by the removal of the solvent on a rotary evaporator. The product was puified by extraction with hexane, followed by chromatography on Florosil. The procedure for the synthesis of this catalyst is described in M. J. Fernandez, et at., J.Am.Chem.Soc. 106, 5458–5463 (1984) the contents of which are incorporate herein by reference. The yield of the $\pi^5$-$C_5Me_5RhH_2(SiEt_3)_2$ catalyst product was 68%(172 mg., 0.365 mmol). The spectroscopic characterization was as follows: $^1$HNMR ($C_6D_6$): δ1.7 (s, 15H), 1.09 (t, J=7.2 Hz, 18H), 0.89 (q, J=7.2 Hz, 12H).

Catalyst Example 8

This example illustrates that synthesis of another embodiment of the catalyst within the scope of the invention.

$[(\eta^6$-$C_6Me_6)Rh(\eta^5$-$C_5Me_5)](PF_6)$ catalyst precursor was synthesized according to the following procedure: Following preparation of the $[C_5Me_5RhCl_2]_2$ intermediate as described in example 1, 195 mg, or 0.316 mmol, of $[C_5Me_5RhCl_2]_2$ and 233 g, or 1.38 mmol, of hexamethylbenzene was combined with 4.5 ml of trifluoroacetic acid. The mixture was refluxed for 7 hours and then cooled to room temperature. Trifluoroacetic acid was removed under vacuum. The resulting white solid was dissolved in 12 mL of water. The slurry was filtered through a medium fritted funnel. An aqueous solution of $NH_4PF_6$ (345 mg., 2.12 mmol) was added to the filtrate to precipitate the catalyst as an off white solid. The solid was collected by filtration and washed with water (3×7 ml) and $Et_2O$ (3×7 ml). The solid was dried under high vacuum and 100° C. for 2 hours.

$[(\eta^4$-$C_6Me_6)Rh(\eta^5$-$C_5Me_5)]$ was synthesized according to the following procedure: 505 mg, 0.731 mmol, of $[(\eta^6$-$C_6Me_6)Rh(\eta^5$-$C_5Me_5)](PF_6)$ was reduced by combining it with 250 mg, 132 mmol, dicyclopentadienyl cobalt in pentane at room tempertare for allowing the stir for 9 hours. The product was isolated by filtration, followed by removal of pentane by evaporation under vacuum.

The yield of the $[(\eta^6$-$C_6Me_6)Rh(\eta^5$-$C_5Me_5)]$ catalyst product was 96%(255 mg., 0.637 mmol). The spectroscopic characterization was as follows: $^1$HNMR ($C_6D_6$): δ2.05 (s, 6H), 1.64 (s. 15H), 1.42 (s, 6H), and 1.28 (s, 6H).

Organoboron Example 9

2-octyl-4,4,5,5-tetramethyl-1,3,2-dioxaborolane was prepared by placing 272 mg, or 2.42 mmol, of 1-octene and 137 mg, or 1.07 mmol, of pinacolborane into an NMR sample tube. The solution was frozen, the system was evacuated under high vacuum, and the sample tube was flame-sealed. The sample was the heated at 120° C. for 14 hours. The reaction vessel was opened in a dry box, and the reaction mixture was passed through a small plug of silica suspended in pentane. The solvent was evaporated under vacuum, providing 2-octyl-4,4,5,5-tetramethyl-1,3,2-dioxaborolane as a clear oil. The yield was 83% (213 mg, 0.885 mmol). This sample was prepared as a reference standard to detect the presence of internal isomers in a functionalization reaction where selectivity towards the primary C—H bond site on the hydrocarbon (octane) is desired. This product was characterized by GC/MS, $^1$H and $^{11}$BNMR.

Organoborane Example 10

2-decyl-4,4,5,5-tetramethyl-1,3,2-dioxaborolane was prepared in the same way as in example 10, except that 1-octene was replaced with 1-decyl, to produce a product yield of 70%.

This sample was prepared as a reference standard to detect the presence of internal isomers in a functionalization reaction where selectivity towards the primary C—H bond site on the hydrocarbon (decane) is desired. This product was characterized by GC/MS, $^1$H and $^{11}$BNMR.

Organoborane Example 11

2-(1-methyl-heptyl)-4,4,5,5-tetramethyl-1,3,2-dioxaborolane was prepared in situ by recting 2.5 g (12.9 mmol) of 2-bromooctane and 0.756 g (31.1 mmol) Mg turnings in anhydrous 10 ml THF at 22° C. The solution was transferred slowly by cannula into a diethyl ether solution of 1.42 g (13.7 mmol) B(OMe)$_3$ with stirring at −72° C. under nitrogen. The solution was reacted at this temperature for 4 hours and was then gradually warmed to room temperature. To the solution was added 10 mL water containing (1.0 mL) $H_2SO_4$. The resulting solution was stirred for 1 hours. The ether layer of the mixture was separated, and the solvent was evaporated under vacuum to provide 894 mg of a white solid.

Without further purification, 553 mg of the crude 2-octylboronic acid was combined with 430 mg of pinacol in THF. The reaction solution was heated at reflux for two days, after which time the solvent was evaporated under vacuum. The resulting crude product was purified by silica gel chromatography, providing a clear oil. The yield of -(1-methyl-heptyl)-4,4,5,5-tetramethyl-1,3,2-dioxaborolane was 22% (426 mg, 1.77 mmol) with respect to 2-bromooctane.

This sample was prepared as a reference standard to detect the presence of internal isomers in a functionalization reaction where selectivity towards the primary C—H bond site on the hydrocarbon (octane) is desired. This product was characterized by GC/MS, $^1$H and $^{11}$BNMR, $^{13}$CNMR, and High Resolution Mass Spectroscopy.

Functionalization Example 12

A commercially available functionalizing reagent 4,4,5,5-tetramethyl-1,3,2-dioxaborolane was reacted with n-decane in the presence of the $\eta^5$-$C_5Me_5$Ir(ethylene)$_2$ catalyst as prepared in example 4 to produce a functionalized decylboryl adduct according to the following equation:

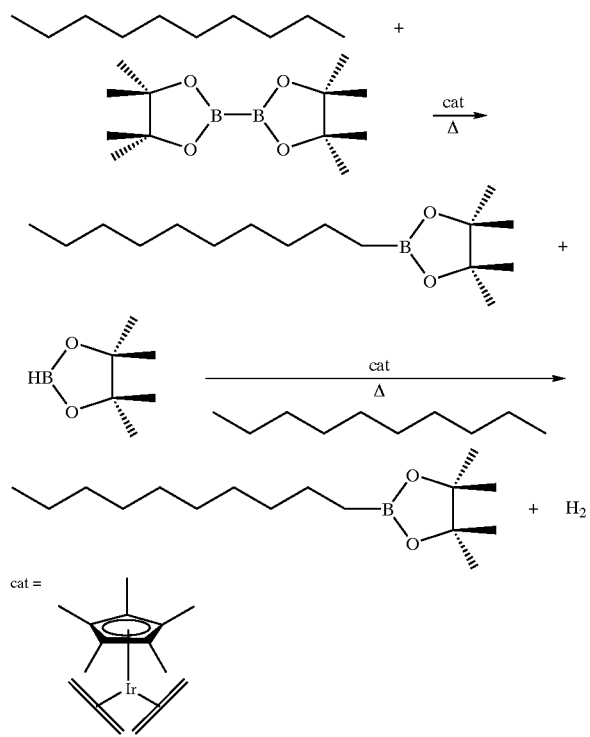

In a dry box, a solution containing 0.0151 mmol of the Cp*Ir(C$_2$H$_2$)$_2$ (Cp*=$\eta^5$ C$_5$Me$_5$) catalyst and 33.6 mg (0.132 mmol) B$_2$pin$_2$ (B$_2$pin$_2$=4,4,5,5-tetramethyl-1,3,2-dioxaborolane) obtained from Callery Chemicals in 0.7 ml of dry n-decane was placed in an NMR sample tube attached to a kontes vacuum adapter using a Cajon Ultratorr connector. The solution was frozen, and the system was evacuated under high vacuum. The sample tube was then flame sealed. The sample was removed from the box and placed in a 190° C. oil bath. The solution was heated for 130 hours at 190° C. and monitored periodically by $^{11}$B NMR spectroscopy. $^{11}$B NMR spectroscopy showed that B$_2$pin$_2$ was completely consumed and that HBpin was formed as accompanying product.

The HBpin sample was then heated at 210° C. for 115 hours, after which time the $^{11}$B NMR spectrometer showed complete consumption of pinacolborane. The sample was brought into the dry box and a solution of dodecahydrotriphenylene (15.2 mg, 0.0632 mmol) in benzene was added. An aliquot was then removed and analyzed by GC. The yield of the 1-decylBpin functionalized product was 46%. 100% of the B$_2$pin$_2$ was reacted. 98% of the HBpin was reacted. The catalyst turnover count was 8. The reaction proceeded slowly as indicated by the amount of time taken to substantially completely convert the B$_2$pin$_2$ functionalizing reagent. Characterization of the 1-decylBpin product by GC/MS and $^1$HNMR revealed functionalization at the primary and terminal C—H bond of decane. The selectivity toward the 1-decylBpin product at the primary C—H bond was exclusive, on the order of 99.9%+. Other decyl by-products were not detected.

Comparative Functionalization Example 12

The same reactants and reaction conditions as used in Example 12 were followed in this comparison example, with the following differences:

The catalyst employed did not contain an unsaturated aliphatic ligand or a 7 arene ligand. Instead, the catalyst used was the $\eta^5$-$C_5Me_5$IrH$_4$ catalyst compound obtained in Catalyst Example 3, having the following structure:

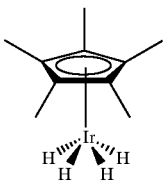

The amount of catalyst employed was 10%, and the reaction mixture was reacted at 170° C. After 4 days, the yield of 1-decylBpin was only 16%, indicating low catalytic activity. It is believed that hydrogen does not readily dissociate from the metal center by application of thermal energy, thereby rendering this compound unsuitable as a catalyst for use in a thermal process.

Functionalization Example 13

The functionalizing reagent 4,4,5,5-tetramethyl-1,3,2-dioxaborolane obtained from Callery Chemicals was reacted with n-octane in the presence of C$_5$Me$_5$Rh(ethylene)$_2$ catalyst as prepared in example 5 to produce a functionalized decylboryl adduct according to the following equation:

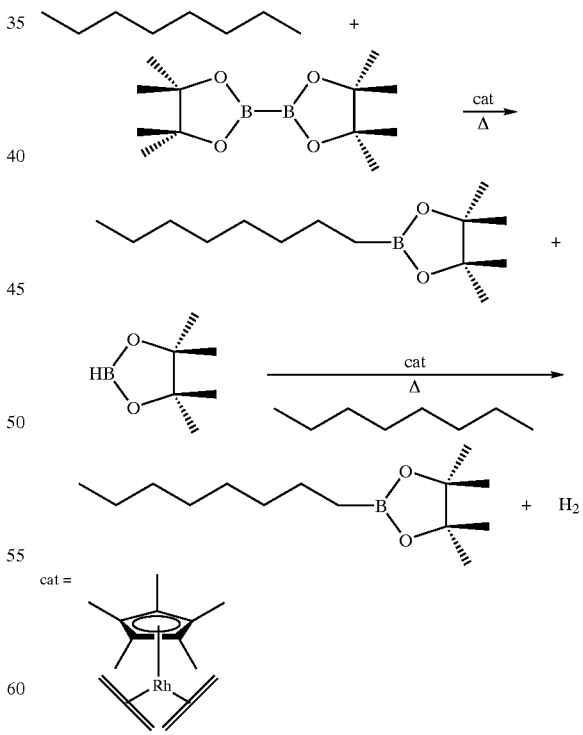

In a dry box, a solution containing 0.00125 mmol of the Cp*Rh(C$_2$H$_2$)$_2$ (CP*=$\eta^5$ C$_5$Me$_5$) catalyst and 31.7 mg (0.125 mmol) B$_2$pin$_2$ (B$_2$pin$_2$=4,4,5,5-tetramethyl-1,3,2-dioxaborolane) obtained from Callery Chemicals in 0.7 ml of dry n-octane was placed in a screw-cap NMR sample tube and sealed tightly. The sample was removed from the box and placed in a 150° C. oil bath. The solution was heated for 80 hours at 150° C. and monitored periodically by $^{11}$B NMR spectroscopy. $^{11}$B NMR spectroscopy showed that HBpin was completely consumed.

The sample was brought into the dry box and a solution of dodecahydrotriphenylene (15.2 mg, 0.0632 mmol) in benzene was added by pipette. An aliquot was then removed and analyzed by GC.

The yield of the 1-octylBpin functionalized product was 72%. 100% of the $B_2pin_2$ was reacted. The catalyst turnover count was 144. The amount of time taken to convert $B_2pin_2$ was 80 minutes. Characterization of the 1-octylBpin product by GC/MS and $^1$HNMR revealed functionalization at the primary and terminal C—H bond of octane. The selectivity toward the 1-octylBpin product at the primacy C—H bond was exclusive, 99.9+%. Other octyl by-product, were not detected.

Functionalization Examples 14–20

The same procedures as set forth in Example 13 was followed in Examples 14–22, except the amounts and type of catalyst, type of hydrocarbon substrate, and time of reaction were varied as set forth in Table 1 below. The catalyst turnover and selectivity to the primary C—H bond position on the hydrocarbon substrate results are also set forth in Table 1. Conversion of $B_2pin_2$ in each case was 100%, except in Example 19, which was 99%. Yields were determined by GC. When benzene was used as the substrate, a solution containing the catalyst was heated at 150° C., and a known amount of dodecahydrotriphenylene was added as an internal standard before or after the reaction. In each example, $B_2pin_2$ was used as the functionalizing reagent in the amounts specified in examples 12–13.

Upon further heating the reaction solution at the same temperature for 5 hours total, HBpin was completely consumed. Analysis of the borane products by GC/MS showed that 1-octylBpin was the only isomer formed by this process. Comparison of the GC/MS of this product with the GC/MS of 2-octylBpin prepared in example 10 revealed that no 2-octylBpin internal isomer was made as a by-product. Other ethylene-boryl by-products derived from the ethylene ligand were detected by GC/MS. Example 16 employed the catalyst from Example 7 containing $(HSiEt_3)$ligands. The reaction rate, however, was slower than that for example 15, and the yields were unsatisfactory.

The functionalization of n-octane in Example 16, using the aromatic $\eta^4$-$C_6Me_6$ ligand on the catalyst, proceeded selectively to the terminal 1-octylBpin product in high yield, at a reaction rate intermediate to the rate in Examples 14 and 15. $^{11}$BNMR spectrometry showed clean conversion of $B_2pin_2$ to the 1-octylBpin and HBpin within 1 hour. Within 25 hours, the HBpin was completely converted to the 1-octylBpin.

The yield and selectivity in Examples 20 and 21 were based on functionalization at the primary C—H bond site on the methyl branch of the methylcyclohexane substrate. Example 19 is shown to demonstrate that a hydrocarbon containing a heteroatom, oxygen, may be selectively and thermally functionalized at a primary C—H bond.

What we claim is:

1. A process for selectively functionalizing a hydrocarbon selected from the group consisting of an aliphatic hydrocarbon, an alkyl branched alicyclic hydrocarbon, and a combination thereof, at a primary saturated C—H hydrocarbon bond, said method comprising thermally reacting a functionalizing reagent and the hydrocarbon in the presence of a catalyst, said catalyst comprising:

a) a transition metal;

TABLE 1

| Example | Hydrocarbon Substrate | Catalyst Example # | Cat. Loading (mole) | Time (h) | Yield of Rbpin | Catalyst Turnover | Selectivity |
|---|---|---|---|---|---|---|---|
| 14 | n-octane | 5 | 5% | 5 | 84% | 34 | 100% |
| 15 | n-octane | 7 | 5% | 90 | 39% | 16 | 100% |
| 16 | n-octane | 8 | 5% | 25 | 88% | 35 | 100% |
| 17 | n-octane | 8 | 1% | 80 | 72% | 144 | 100% |
| 18 | n-octane | 6 | 5% | 27 | 53% | 21 | 100% |
| 19 | n-butyl ether | 8 | 4% | 80 | 64% | 32 | 100% |
| 20* | 2-methyl heptane | 8 | 1% | 60 | 61% | 122 | 100% terminal, 5:1 for less hindered methyl group |
| 21 | 2-methyl heptane | 5 | 2.5% | 30 | 73% | 58 | Same as 20 |

*2-Methylheptane possesses two types of primary C—H bonds. The reaction leads to preferential reaction at the less hindered methyl group to provide a 5:1 ratio of the two terminal functionalization products.

In example 14, reaction of octane with $B_2pin_2$ at 150° C. for 50 minutes gave complete conversion of $B_2pin_2$ to octylbpin and HBpin. In this case, the yield of octylBpin was higher than the amount of converted diboron reagent, suggesting that the reaction of HBpin with octane was also occuring, but at a slower rate than the reaction of $B_2pin_2$.

b) a 3 to 8, cyclic or non-cyclic, aromatic or non-aromatic, neutral, cationic or anionic substituted or unsubstituted electron donor moiety which does not dissociate under thermal reaction conditions, wherein said moiety
(i) lacks aromatic C—H bonds on the moiety directly bonded to the transition metal, or (ii) contains sterically hindered aromatic C—H bonds on the moiety directly bonded to the transition metal; and c) a source of ligands adapted to formally donate an electron pair to the transition metal a) and which dissociate thermally; and wherein said functionalizing reagent comprises boron.

2. The process of claim 1, comprising functionalizing an aliphatic compound, wherein selectivity to functionalizing said aliphatic compound at a primary C—H bond is 90% or more.

3. The process of claim 2, comprising functionalizing an alkane comprising a terminal C—H bond, wherein selectivity to functionalizing the alkane at the terminal C—H bond is 95% or more.

4. The process of claim 3, wherein the selectivity to functionalizing the alkane at the terminal C—H bond is 98% or more.

5. The process of claim 4, wherein the selectivity to functionalizing the alkane at the terminal C—H bond is 99% or more.

6. The process of claim 1 wherein the transition metal is adapted to traverse 4 or more oxidation states.

7. The process of claim 1, wherein the transition metal comprises Rh or Ir.

8. The process of claim 1 wherein the transition metal comprises Rh, and the hydrocarbon comprises an alkane.

9. The process of claim 1 wherein said b) moiety comprises an electronic charge which fully stabilizes the transition metal.

10. The process of claim 1, wherein the b) moiety comprises a cyclic fully substituted aromatic moiety.

11. The process of claim 1, wherein the b) moiety comprises a fully substituted $\eta^5-\eta^6$ cyclic moiety having a 5–8 carbon membered ring.

12. The process of claim 1, wherein the b) moiety comprises a fully substituted $\eta^5$ cyclopentadienyl moiety.

13. The process of claim 12, wherein said moiety comprises a $\eta^5$ pentamethylcyclopentadienyl moiety.

14. The process of claim 1 wherein the b) moiety comprises $C_1$–$C_4$ alkyl substituted cyclopentadienyl compounds.

15. The process of claim 14 wherein the b) moiety comprises a cyclopentadienyl compound substituted with from one to five moieties selected from the group consisting of methyl, propyl, isopropyl, t-butyl groups, and combinations thereof.

16. The process of claim 15, wherein said b) moiety comprises a dimethylcyclopentadienyl, methylcyclopentadienyl, tetramethylcyclopentadienyl, diethylcyclopentadienyl, t-butylcyclopentadienyl, or pentamethylcyclopentadienyl compound.

17. The process of claim 1, wherein said b) moiety is selected from the group consisting of a hydroxyl group, $C_1$–$C_4$ alkyl substituted indenyl or fluorenyl groups, and combinations thereof.

18. The process of claim 1, wherein the b) moiety contains no aromatic C—H bonds.

19. The process of claim 18, wherein the b) moiety is fully substituted with $C_1$–$C_4$ alkyl groups.

20. The process of claim 1, wherein the b) moiety is selected from the group consisting of a methylcyclopentadiene, ethylcyclopentadiene, t-butylcyclopentadiene, hexylcyclopentadiene, octylcyclopentadiene, 1,2-dimethylcyclopentadiene, 1,3-dimethylcyclopentadiene, 2,4-dimethyl-$\eta^5$-pentadien-1-yl, 1,5-dimethyl-$\eta^5$-pentadien-2-yl, 2,4-dimethyl-$\eta^5$-pentadien-3-yl, 1,5-dimethyl-$\eta^5$-pentadien-3-yl, 1,2,4-trimethylcyclopentadiene, pentamethylcyclopentadiene, 1,5-bis(trimethylsilyl)-$\eta^5$-pentadien-3-yl, 1,2,3,4-tetramethylcyclopentadiene, 1,2,6,6-tetramethyl-$\eta^5$-cyclohexadien-4-yl, 1,2,4,6,6-pentamethyl-$\eta^5$-cyclohexadien-3-yl, 1,2,4,6,6-pentamethyl-$\eta^5$-cyclohexadien-5-yl, 1,2,5,6,6-pentamethyl-$\eta^5$-cyclohexadien-4-yl, 1,2,4,5,6,6-hexamethyl-$\eta^5$-cyclohexadien-3-yl; 1,2,4,5-tetramethyl-6,6-cyclotrimethylene-$\eta^5$-cyclohexadien-3-yl; 1,2-dihydronaphthalen-1-yl; 1,2-dihydronaphthalen-2-yl; 1,1-dimethyl-1,2-dihydronaphthalen-2-yl; 1,1-dimethyl-1,2-dihydronaphthalen-4-yl; diphenylmethyl-di(1-cyclohexenyl)methyl; 1,1-dimethyl-1,2,5,6,7,8-hexahydronaphthalen-4-yl; 1,1-dimethyl-1,4,5,6,7,8-hexahydronaphthalen-4-yl; 1,1-dimethyl-1,5,6,7,8,9-hexahydronaphthalen-4-yl; 1,1,2,3-tetramethyl-1,2,5,6,7,8-hexahydronaphthalen-4-yl; 1,1,2,3-tetramethyl-1,4,5,6,7,8-hexahydronaphthalen-4-yl; 1,1,2,3-tetramethyl-1,5,6,7,8,-hexahydronaphthalen-4-yl; 8,9,-hexahydronaphthalen-9,10-dihydroanthracen-9-yl; 9,10-dihydroanthracen-1-yl; 9,9-dimethyl-9,10-dihydroanthracen-10-yl; 1,2,3,4,9,10-hexahydroanthracen-9-yl; 1,2,3,4,9,10-hexahydroanthracen-1-yl; 1,2,3,4,9,11-hexahydroanthracen-9-yl; 1,4,5,8,9,10-hexahydroanthracen-1-yl; 9,9-dimethyl-1,4,5,8,9,10-hexahydroanthracen-10-yl; 9,9-dimethyl-1,4,5,8,9,10-hexahydroanthracen-2-yl; 8,8-dimethyl-1,4,5,8,9,10-hexahydroanthracen-10-yl; 1,2,3,4,5,6,7,8,9,10-decahydroanthracen-9-yl; 1,2,3,4,5,6,7,8,9,11-decahydroanthracen-9-yl; 9,9-dimethyl-1,2,3,4,5,6,7,8,9,10-decahydroanthracen-10-yl; 9,9-dimethyl-1,2,3,4,5,6,7,8,9,11-decahydroanthracen-10-yl, 4,7-dimethylindene, 4,5,6,7-tetrahydroindene; 3-methylcyclopentadienylsilane, 1,2-dimethylcyclopentadienylsilane, 1,3-dimethylcyclopentadienylsilane, 1,2,4-trimethylcyclopentadienylsilane, 1,2,3,4-tetramethylcyclopentadienylsilane, pentamethylcyclopentadienylsilane, 1,2,4-trimethylindenylsilane, 1,2,3,4-tetramethylindenylsilane or pentamethylindenylsilane group.

21. The process of claim 1, wherein the c) ligand comprises aliphatic unsaturated or π arene compounds, said π arene compounds lacking π arene C—H bonds.

22. The process of claim 1, wherein the c) ligand has a structure selected from the group consisting of one of the following structural formulas:

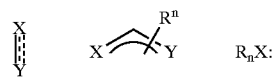

wherein X and Y independently are selected from the group consisting of bridged groups and unbridged groups comprising an element selected from the group consisting of H, C, B, S, N, Si, Sn, P, and As, and combinations thereof, R is selected from the group consisting of hydrogen and substituents adapted to cause the c) ligand to formally donate an electron pair to the transition metal a) and to dissociate thermally, and n represents an integer ranging from 0 to 8.

23. The process of claim 1 wherein the c) ligand is represented by the following structural formula:

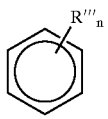

wherein R''' independently is selected from the group consisting of hydrogen, alkyl groups selected from the group consisting of saturated and unsaturated, branched and unbranched alkyl groups having from 1 to 15 carbon atoms, alkaryl groups comprising one ring or more than one fused ring and comprising alkyl groups selected from the group consisting of saturated and unsaturated, branched and unbranched alkyl groups having from 1 to 15 carbon atoms, and n represents the number of R''' groups and is an integer ranging from 2 to 6.

24. The process of claim 22, wherein unsaturation exists between X and Y, said unsaturation being olefinic or aromatic.

25. The process of claim 1, wherein the c) ligand comprises a linear or branched aliphatic olefinic group having from 2 to 8 carbon atoms.

26. The process of claim 25, wherein the c) ligand comprises ethylene, propylene, 1-butene, 2-butene, 1-pentene, 2-pentene, isopentene, hexene-1, 2-hexene, 3-hexene, 4-methylpentene-1, 2-methylpentene-1, 4-methylbutene-1, 1-heptene, 2-heptene, 3-heptene, 1-octene, 2-octene, 2-methylheptene-1, 4-octene, or 3,4-dimethyl-3-hexene groups.

27. The process of claim 26, wherein the aliphatic olefinic group comprises ethylene.

28. The process of claim 1, wherein the c) ligand comprises allyl acrylate, 2-propen-1-ol, allylamine, allylbromide, allyl hexanoate, allyl cyanide, allyl carbonate, 1-allyl-4-hydroxybenzene, allyl-alpha-ionone, allyl isocyanate, allyl isothiocyanate, allyl thiol, allyl methacrylate, 4-allyl-2-methoxyphenol, 4-allyl-1,2-methylenedioxybenzene, allyl pelargonate, allyl sulfide, or allyl thiourea groups.

29. The process of claim 1, wherein the c) ligand comprises a π-arene group comprising divinylbenzene, p-xylene, 1,3,5-trimethylbenzene (mesitylene), 1,2,4-trimethylbenzene, 1,3,5-triisopylbenzene, 1,2,3,4-tetramethylbenzene, 1,2,3,5-tetramethylbenzene, 1,2,4,5-tetramethylbenzene (durene), pentamethylbenzene, hexamethylbenzene, fluorene, dibenzostannepine, tellurophene, phenothiarsine, selenanthrene, phenoxaphosphine, phenarsazine, phenatellurazine, 1,2 3 4,4a,9a)-9-(phenylmethylidene)fluorene, or a (1,2 3,4,4a, 9a)-9-(3-phenyl-2-propenylidene)fluorene group.

30. The process of claim 1, wherein the c) ligand comprises tolyl, p-ethylbenzyl, p-isopropylbenzyl, p-propylbenzyl, p-t-butylbenzyl, 1,3,5-trimethylbenzyl (mesitylene), 1,2,4-trimethylbenzyl, 1,3,5-triisopylbenzyl, 1,2,3,4-tetramethylbenzyl, 1,2,3,5-tetramethylbenzyl, 1,2,4,5-tetramethylbenzyl ,(durene), pentamethylbenzyl, hexamethylbenzyl, or di-t-butylbenzene.

31. The process of claim 30, wherein the c) ligand comprises a $C_6$ compound substituted with three to six $C_1$–$C_4$ alkyl groups.

32. The process of claim 31, wherein the c) ligand comprises an $\eta^4$ hexamethylbenzyl group.

33. The process of claim 1, wherein said functionalizing reagent comprises a boron alkyl, boron aryl, boron hydride, organoboron hydride, or organoboron halide group.

34. The process of claim 33, wherein said functionalizing reagent is a haloboryl compound represented by any one of the following structures:

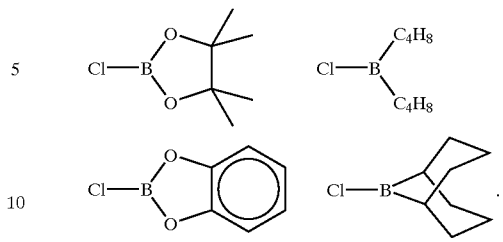

35. The process of claim 1, wherein the functionalizing reagent comprises a dioxadiborolane compound.

36. The process of claim 1, wherein the functionalizing reagent comprises a diaza-, dithia-, dioxa-, oxa-, azaborolane, borinane, or diboron compound.

37. The process of claim 31, wherein the functionalizing reagent comprises a diboron moiety represented by the following structural formula:

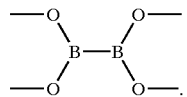

38. The process of claim 37, wherein the functionalizing reagent comprises a diboron compound represented by the following structural formula:

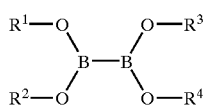

wherein $R^1$, $R^2$, $R^3$, and $R^4$ independently are selected from the group consisting of linear and branched, unsubstituted and halogen substituted, alkyl groups having from 1 to 24 carbon atoms, alkoxy groups having from 3 to 24 carbon atoms, cycloaliphatic groups having from 3 to 8 carbon atoms, and aryl groups having from 5 to 16 atoms wherein $R^1$ and $R^2$ are unfused or fused and $R^2$ and $R^3$ are unfused or fused.

39. The process of claim 38, wherein the functionalizing reagent comprises pinacolborane, bis-pinacolate diboron or bis(t-butylcatecholate) diboron.

40. The process of claim 1, wherein the functionalizing reagent and the hydrocarbon are reacted in the presence of said catalyst at a temperature ranging from 70° C. to 250° C.

41. The process of claim 35, wherein the functionalizing reagent and the hydrocarbon are reacted in the presence of a catalyst at a temperature ranging from 100° C. to 200° C. in the absence of photolytic activation of the catalyst.

42. The process of claim 1, wherein the molar ratio of functionalizing reagent to catalyst is greater than 10:1.

43. The process of claim 42, wherein the molar ratio of functionalizing reagent to catalyst is greater than 200:1.

44. The process of claim 1, wherein the catalyst turns over 50 times or more.

45. The process of claim 44, wherein the catalyst turns over 100 times or more in the absence of a sacrificial hydrogen acceptor.

46. The process of claim 1, wherein the catalyst is soluble in the hydrocarbon, said hydrocarbon comprising an alkane.

47. A catalytic process having more than 50 turnovers comprising thermally activating said catalyst in the presence of a functionalizing reagent and a hydrocarbon selected from the group consisting of an aliphatic hydrocarbon, an alkyl branched alicyclic hydrocarbon, and a combination thereof, said catalyst comprising:

a) a transition metal;

b) a 3 to 8, cyclic or non-cyclic, aromatic or non-aromatic, neutral, cationic or anionic, substituted or unsubstituted electron donor moiety which does not dissociate under thermal reaction conditions, wherein said moiety (i) lacks aromatic C—H bonds on the moiety directly bonded to the transition metal, or (ii) contains sterically hindered aromatic C—H bonds on the moiety directly bonded to the transition metal; and c) a source of ligands adapted to formally donate an electron pair to the transition metal a) and which dissociate thermally;

and wherein said functionalizing reagent comprises an element selected from the group consisting of B, C, N, 0, Si, P, Si, Ge, As, Al, or Se.

48. The process of claim 47 wherein said hydrocarbon is an aliphatic compound comprising a primary C—H bond.

49. The process of claim 48 wherein selectivity to functionalizing the aliphatic compound at said primary C—H bond is 90% or more.

50. The process of claim 49 wherein said aliphatic compound is an alkane comprising a terminal C—H bond, wherein selectivity to functionalizing the alkane at the terminal C—H bond is 95% or more.

51. The process of claim 50, wherein the selectivity to functionalizing the alkane at the terminal C—H bond is 98% or more.

52. The process of claim 47, wherein the transition metal comprises Rh.

53. The process of claim 47, wherein the b) moiety comprises a fully substituted $\eta^5$–$\eta^6$ cyclic moiety having a 5–8 carbon membered ring.

54. The process of claim 53, wherein the b) moiety comprises a fully substituted $\eta^5$ cyclopentadienyl moiety.

55. The process of claim 54, wherein said moiety comprises a $\eta^5$ pentamethylcyclopentadienyl moiety.

56. The process of claim 47, wherein the b) moiety comprises a cyclopentadienyl compound substituted with from one to five moeities selected from the group consisting of methyl, propyl, isopropyl, t-butyl groups, and combinations thereof.

57. The process of claim 47, wherein said b) moiety comprises a dimethylcyclopentadienyl, methylcyclopentadienyl, tetramethylcyclopentadienyl, diethylcyclopentadienyl, t-butylcyclopentadienyl, or pentamethylcyclopentadienyl group.

58. The process of claim 47, wherein the b) moiety contains no aromatic C—H bonds.

59. The process of claim 47, wherein the c) ligand comprises aliphatic unsaturated or π arene compounds, said n arene compounds lacking π arene C—H bonds.

60. The process of claim 59, wherein the c) ligand is represented by the following structural formula:

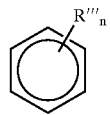

wherein R''' independently is selected from the group consisting of hydrogen, alkyl groups selected from the group consisting of saturated and unsaturated, branched and unbranched alkyl groups having from 1 to 15 carbon atoms, alkaryl groups comprising one ring or more than one fused ring and comprising alkyl groups selected from the group consisting of saturated and unsaturated, branched and unbranched alkyl groups having from 1 to 15 carbon atoms, and n represents the number of R''' groups and is an integer ranging from 2 to 6.

61. The process of claim 60, wherein R''' represents a saturated, branched or unbranched alkyl group having from 1 to 4 carbon atoms.

62. The process of claim 47, wherein the c) ligand comprises a linear or branched aliphatic olefinic group having from 2 to 8 carbon atoms.

63. The process of claim 62, wherein the c) ligand comprises ethylene, propylene, 1-butene, 2-butene, 1-pentene, 2-pentene, isopentene, hexene-1, 2-hexene, 3-hexene, 4-methylpentene-1, 2-methylpentene-1, 4-methylbutene-1, 1-heptene, 2-heptene, 3-heptene, 1-octene, 2-octene, 2-methylheptene-1, 4-octene, or 3,4-dimethyl-3-hexene groups.

64. The process of claim 63, wherein the aliphatic group comprises ethylene.

65. The process of claim 47, wherein the c) ligand comprises a tolyl, p-ethylbenzyl, p-isopropylbenzyl, p-propylbenzyl, p-t-butylbenzyl, 1,3,5-trimethylbenzyl (mesitylene), 1,2,4-trimethylbenzyl, 1,3,5-triisopylbenzyl, 1,2,3,4-tetramethylbenzyl, 1,2,3,5-tetramethylbenzyl, 1,2,4,5-tetramethylbenzyl (durene), pentamethylbenzyl, hexamethylbenzyl, or di-t-butylbenzene group.

66. The process of claim 47, wherein the c) ligand comprises a $C_6$ group substituted with a three to six $C_1$–$C_4$ alkyl groups.

67. The process of claim 66, wherein the c) ligand comprises an $\eta^4$ hexamethylbenzyl group.

68. The process of claim 47, wherein said functionalizing reagent comprises boron.

69. The process of claim 68, wherein said functionalizing reagent comprises a boron alkyl, boron aryl, boron hydride, organoboron hydride, or organoboron halide group.

70. The process of claim 47, wherein said functionalizing reagent is a haloboryl compound represented by any one of the following structures:

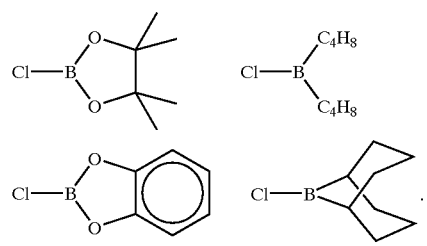

71. The process of claim 47, wherein the functionalizing reagent comprises a dioxadiborolane compound.

72. The process of claim 47, wherein the functionalizing reagent comprises a diaza-, dithia-, dioxa-, oxa-, azaborolane, borinane, or diboron compound.

73. The process of claim 47, wherein the functionalizing reagent comprises a diboron moiety represented by the following structural formula:

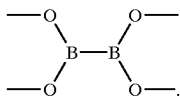

74. The process of claim 73, wherein the functionalizing reagent comprises a diboron compound represented by the following structural formula:

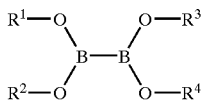

wherein $R^1$, $R^2$, $R^3$, and $R^4$ independently are selected from the group consisting of linear and branched, unsubstituted and halogen substituted, alkyl groups having from 1 to 24 carbon atoms, alkoxy groups having from 3 to 24 carbon atoms, cycloaliphatic groups having from 3 to 8 carbon atoms, and aryl groups having from 5 to 16 atoms wherein $R^1$ and $R^2$ are unfused or fused and $R^2$ and $R^3$ are unfused or fused.

75. The process of claim 74, wherein the functionalizing reagent comprises pinacolborane, bis-pinacolate diboron or bis(-butylcatecholate)diboron.

76. The process of claim 47, wherein the functionalizing reagent and the hydrocarbon are reacted in the presence of said catalyst at a temperature ranging from 70° C. to 250° C.

77. The process of claim 76, wherein the functionalizing reagent and the hydrocarbon are reacted in the presence of a catalyst at a temperature ranging from 100° C. to 200° C.

78. The process of claim 47, wherein the molar ratio of functionalizing reagent to catalyst is greater than 200:1.

79. The process of claim 78, wherein the catalyst turns over 100 times or more.

80. The process of claim 47, wherein said functionalization is conducted in the absence of a sacrificial hydrogen acceptor.

81. The process of claim 47, wherein the catalyst is soluble in the hydrocarbon, said hydrocarbon comprising an alkane.

82. A functionalization process comprising selectively functionalizing 80% or more of primary C—H hydrocarbon bonds in a hydrocarbon composition by thermally activating a catalyst, wherein the catalyst in said process is turned over 50 or more times.

83. The process of claim 82, wherein the catalyst comprises:
   a) Rh or Ir;
   b) a fully substituted cyclic $C_5$ moiety having a π-coordinated electronic structure and lacking aromatic C—H bonds; and
   c) ligands comprising aliphatic unsaturated or π arene compounds, and wherein said π arene compounds
      (i) lack aromatic C—H bonds on the moiety directly bonded to the transition metal, or
      (ii) contain sterically hindered aromatic C—H bonds on the moiety directly bonded to the transition metal.

84. The process of claim 83, said catalyst comprises Rh.

85. The process of claim 83, said source of c) ligands comprising unsaturated aliphatic compounds.

86. The process of claim 83, said b) moiety comprises a fully substituted $\eta^5$ cyclopentadienyl moiety.

87. The process of claim 86, wherein said b) moiety comprises an $\eta^5$ pentamethylcyclopentadienyl moiety.

88. The process of claim 83, wherein said catalyst comprises Rh, said b) moeity comprises a cyclopentadienyl compound substituted with from one to five moieties selected from the group consisting of methyl, propyl, isopropyl, t-butyl groups, and combinations thereof, and said c) ligand is represented by the following structural formula:

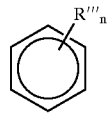

wherein R''' independently is selected from the group consisting of hydrogen, alkyl groups selected from the group consisting of saturated and unsaturated, branched and unbranched alkyl groups having from 1 to 15 carbon atoms, alkaryl groups comprising one ring or more than one fused ring and comprising alkyl groups selected from the group consisting of saturated and unsaturated, branched and unbranched alkyl groups having from 1 to 15 carbon atoms, and n represents the number of R''' groups and is an integer ranging from 2 to 6.

89. The process of claim 83, wherein said catalyst comprises Rh, said b) moeity comprises a cyclopentadienyl compound substituted with from one to five moieties selected from the group consisting of methyl, propyl, isopropyl, t-butyl groups, and combinations thereof, and said c) ligand comprises a linear or branched aliphatic olefinic group having from 2 to 8 carbon atoms.

90. The process of claim 89, wherein the c) ligand comprises ethylene, propylene, 1-butene, 2-butene, 1-pentene, 2-pentene, isopentene, hexene-1, 2-hexene, 3-hexene, 4-methylpentene-1, 2-methylpentene-1, 4-methylbutene-1, 1-heptene, 2-heptene, 3-heptene, 1-octene, 2-octene, 2-methylheptene-1, 4-octene, or 3,4-dimethyl-3-hexene.

91. The process of claim 82, wherein said hydrocarbon comprises an aliphatic hydrocarbon.

92. The process of claim 91, wherein said aliphatic compounds comprises an alkane comprising n-hexane, n-heptane, n-octane, n-nonane, n-dodecane, n-tridecane, n-tetradecane, n-pentadecane, n-hexadecane, n-heptadecane, n-octadecane, n-nonadecane, n-eicosane, 2,2,3,3-tetra-methylbutane, 2,2,4-trimethylpentane, n-tricontane, or 2-methyl or 2-ethyl $C_6$–$C_{28}$ alkanes.

93. The process of claim 82, comprising functionalizing an alkane, wherein selectivity to functionalizing the alkane at a primary C—H bond is 98% or more.

94. The process of claim 82, comprising a functionalizing reagent, said functionalizing reagent comprising boron.

95. The process of claim 94, wherein said source of boron is represented by the following structural formula:

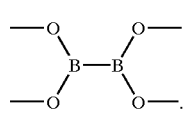

96. The process of claim 95, wherein the functionalizing reagent comprises a diboron compound represented by the following structural formula:

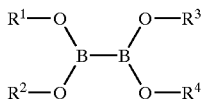

wherein $R^1$, $R^2$, $R^3$, and $R^4$ independently are selected from the group consisting of linear and branched, unsubstituted and halogen substituted alkyl groups having from 1 to 24 carbon atoms, alkoxy groups having from 3 to 24 carbon atoms, cycloaliphatic groups having from 3 to 8 carbon atoms, and aryl groups having from 5 to 16 atoms wherein $R^1$ and $R^2$ are unfused or fused and $R^2$ and $R^3$ are unfused or fused.

97. The process of claim 96, wherein the functionalizing reagent comprises bis-pinacolate diboron or bis(t-butylcatecholate) diboron.

98. The process of claim 82, wherein the hydrocarbon is functionalized in the presence of said catalyst at a temperature ranging from 70° C. to 250° C.

99. The process of claim 98, comprising a functionalizing reagent, wherein the molar ratio of functionalizing reagent to catalyst is greater than 200:1.

100. The process of claim 82, wherein the catalyst turns over 100 times or more, and the hydrocarbon comprises an alkane.

101. A functionalization process comprising selectively functionalizing 80% or more of primary C—H hydrocarbon bonds in a hydrocarbon composition in the presence of a thermally activated catalyst and a functionalizing reagent, wherein said functionalizing reagent comprises a compound containing a moiety represented by the following structure:

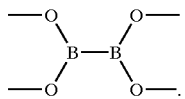

102. The process of claim 101, wherein said hydrocarbon comprises an aliphatic compound.

103. The process of claim 101, wherein the functionalizing reagent comprises a diboron compound represented by the following structural formula:

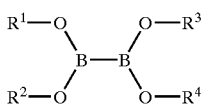

wherein $R^1$, $R^2$, $R^3$, and $R^4$ independently are selected from the group consisting of linear and branched, unsubstituted and halogen substituted alkyl groups having from 1 to 24 carbon atoms, alkoxy groups having from 3 to 24 carbon atoms, cycloaliphatic groups having from 3 to 8 carbon atoms, and aryl groups having from 5 to 16 atoms wherein $R^1$ and $R^2$ are unfused or fused and $R^2$ and $R^3$ are unfused or fused.

104. The process of claim 103, wherein each $R_1$ group attached to the same boron atom through oxygen atoms are fused or bridged through any of said alkyl, alkoxy, cycloaliphatic or aryl groups.

105. The process of claim 104, wherein said diboron compound comprises bis-pinacolate diboron or bis(t-butylcatecholate) diboron.

106. The process of claim 101, comprising thermally activating said catalyst at a temperature ranging from 70° C. to 250° C.

* * * * *

UNITED STATES PATENT AND TRADEMARK OFFICE
CERTIFICATE OF CORRECTION

PATENT NO.     : 6,451,937 B1
DATED          : September 17, 2002
INVENTOR(S)    : John F. Hartwig, Thomas C. Semple and Huiyuan Chen It is certified that error appears in the above-identified patent and that said Letters Patent is hereby corrected as shown below:

<u>Title page,</u>
Item [56], OTHER PUBLICATIONS, please add the following references:
-- "Redox-Induced Hapticity Changes: Effect of Substituents on Arene Bending in a Series of Rhodium Complexes," by Walter J. Bowyer, Jon W. Merkert, and William E. Gelger, <u>Organometallics</u> 1989, 8, pp. 191-198.

"First Synthesis of Bis[1,2,3]Triazolo[1,5-b;5',1'-*f* ][1,3,6]Thiadiazepine Derivatives by [2+1]Condensation of 1,2,3-Thiadiazoles With Vicinal Diamines," by Natalya N. Volkova, Evgeniy V. Tarasov, Wim Dehaen, and Vasiliy A. Bakulev, <u>J. Am. Chem. Soc.</u> 1999, 121, pp. 4086-4087.

"Dehydrogenation of *n*-Alkanes Catalyzed by Iridium "Pincer" Complexes: Regioselective Formation of α-Olefins," by Fuchen Liu, Esther B. Pak, Bharat Singh, Craig M. Jensen, and Alan S. Goldman, <u>J. Am. Chem. Soc.</u> 1999, 121, pp. 4086-4087.

"Mild and Stereoselective Hydroborations of Functionalized Alkynes and Alkenes Using Pinacolborane," by Charles E. Tucker, Jessica Davidson, and Paul Knochel, <u>J. Org. Chem.</u> 1992, 57, pp. 3482-3485.

"Hydrogen/Deuterium Exchange Reactions and Transfer Hydrogenations Catalyzed by [$C_5Me_5Rh(olefin)_2$] Complexes: Conversion of Alkoxysilanes to Silyl Enolates," by Christian P. Lenges, Peter S. White, and Maurice Brookhart, <u>J. Am. Chem. Soc.</u> 1999, 121, pp. 4385-4396. --

Signed and Sealed this

Eighteenth Day of February, 2003

JAMES E. ROGAN
*Director of the United States Patent and Trademark Office*